(12) United States Patent
Zhang et al.

(10) Patent No.: US 10,154,818 B2
(45) Date of Patent: Dec. 18, 2018

(54) BIOMETRIC AUTHENTICATION METHOD AND APPARATUS

(71) Applicant: Samsung Electronics Co., Ltd., Suwon-si (KR)

(72) Inventors: Chao Zhang, Beijing (CN); Xuetao Feng, Beijing (CN); Yang Liu, Beijing (CN); Chisung Bae, Yongin-si (KR); Sang-joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 132 days.

(21) Appl. No.: 14/884,004

(22) Filed: Oct. 15, 2015

(65) Prior Publication Data
US 2016/0183812 A1    Jun. 30, 2016

(30) Foreign Application Priority Data

Dec. 24, 2014  (CN) .......................... 2014 1 0816701
May 12, 2015  (KR) .......................... 10-2015-0066256

(51) Int. Cl.
*A61B 5/0205* (2006.01)
*A61B 5/00* (2006.01)
*A61B 5/117* (2016.01)
*G07C 9/00* (2006.01)

(52) U.S. Cl.
CPC ............ *A61B 5/7246* (2013.01); *A61B 5/117* (2013.01); *G07C 9/00158* (2013.01); *A61B 5/7267* (2013.01); *A61B 2560/0462* (2013.01); *A61B 2562/06* (2013.01); *G07C 2209/14* (2013.01)

(58) Field of Classification Search
CPC ............ G07C 9/00158; G07C 2209/14; A61B 5/7246; A61B 5/117; A61B 5/7267; A61B 2562/06; A61B 2560/0462

USPC ........................................................ 713/186
See application file for complete search history.

(56) References Cited

U.S. PATENT DOCUMENTS

| | | | |
|---|---|---|---|
| 5,719,950 A * | 2/1998 | Osten ................... | A61B 5/0205 340/5.82 |
| 2003/0135097 A1 | 7/2003 | Wiederhold et al. | |
| 2007/0299322 A1 | 12/2007 | Miyajima et al. | |
| 2012/0230555 A1* | 9/2012 | Miura ................ | G06K 9/00087 382/124 |
| 2014/0135631 A1 | 5/2014 | Brumback et al. | |

(Continued)

FOREIGN PATENT DOCUMENTS

| CN | 1672357 A | 9/2005 |
|---|---|---|
| CN | 104054038 B | 3/2018 |

(Continued)

OTHER PUBLICATIONS

Extended European Search Report dated May 2, 2016 in counterpart European Application No. 15193235.7 (7 Pages in English).

(Continued)

*Primary Examiner* — Brandon S Hoffman
*Assistant Examiner* — Nega Woldemariam
(74) *Attorney, Agent, or Firm* — NSIP Law

(57) ABSTRACT

A biometric authentication apparatus and method are provided. The biometric authentication apparatus may obtain at least two types of biosignals, extract a same type of physiological features from each of the biosignals, and determine whether the biosignals are generated from a same living body based on the extracted same type of physiological features.

30 Claims, 14 Drawing Sheets

(56) References Cited

U.S. PATENT DOCUMENTS

| | | | |
|---|---|---|---|
| 2014/0188770 A1 | 7/2014 | Agrafioti et al. | |
| 2014/0304792 A1 | 10/2014 | Derchak et al. | |
| 2015/0317855 A1* | 11/2015 | Sezan | G07C 9/00158 340/5.52 |
| 2016/0087952 A1* | 3/2016 | Tartz | H04W 12/06 455/411 |

FOREIGN PATENT DOCUMENTS

| | | |
|---|---|---|
| JP | 2011-110181 A | 6/2011 |
| JP | 2012-210236 A | 11/2012 |
| KR | 10-2011-0002373 A | 1/2011 |
| KR | 10-2012-0131043 A | 12/2012 |
| KR | 10-2013-0055730 A | 5/2013 |
| KR | 10-2013-0129744 A | 11/2013 |
| WO | WO 2014/157896 A1 | 2/2014 |

OTHER PUBLICATIONS

Chinese Office Action dated Jul. 18, 2018 in corresponding Chinese Patent Application No. 201410816701.2 (11 pages in English, 8 pages in Chinese).

\* cited by examiner

BIOMETRIC AUTHENTICATION METHOD AND APPARATUS

CROSS-REFERENCE TO RELATED APPLICATION(S)

This application claims the benefit under 35 USC 119(a) of Chinese Patent Application No. 201410816701.2, filed on Dec. 24, 2014, in the State Intellectual Property Office of China, and Korean Patent Application No. 10-2015-0066256, filed on May 12, 2015, in the Korean Intellectual Property Office, the entire disclosures of which are incorporated herein by reference for all purposes.

BACKGROUND

1. Field

The following description relates to a method and apparatus to perform a biometric authentication.

2. Description of Related Art

Due to the development of sensor manufacturing and machine learning technologies for pattern identification, technologies for identifying features of living bodies has become more widely diffused and developed. However, to prevent successful identity authentications based on stolen or forged biometric features, there may be a desire for an identity authentication technology that verifies that biometric features are generated from a real living body using a biometric detection function.

Current authentication technologies may include biometric detection schemes that are based on various types of software or hardware. Among authentication technologies, it has been found that schemes using various biometric features may have a relatively high anti-forgery capacity. For example, one of these biometric features may include a signal, such as an electrocardiogram (ECG) signal, that is generated in a living body and that is difficult to be copied or forged. However, it is still possible for an unauthorized person to pass an identity authentication using various biometric features that may each be forged or copied. Therefore, there is a desire to enhance the reliability of identity authentication systems to make it more difficult to pass identity authentication using biometric features that are forged or copied.

SUMMARY

This Summary is provided to introduce a selection of concepts in a simplified form that are further described below in the Detailed Description. This Summary is not intended to identify key features or essential features of the claimed subject matter, nor is the Summary intended to be used as an aid in determining the scope of the claimed subject matter.

One or more embodiments include a biometric authentication method that includes extracting a same physiological feature from each of at least two different type biosignals, and determining whether the biosignals are generated from a same living body based on a comparison of the extracted physiological features.

The method may further include capturing each of the biosignals at a same time using one or more sensors configured to capture biometric features from a body.

The capturing of the biosignals may include controlling the one or more sensors to measure the biosignals for a predetermined period of time.

The biosignals may be different types of biosignals from among a human facial image biosignal type, a fingerprint image biosignal type, a palm print image biosignal type, a blood vessel image biosignal type, an iris image biosignal type, a retinal image biosignal type, an ECG signal biosignal type, an EEG signal biosignal type, a photoplethysmogram (PPG) signal biosignal type, a blood pressure signal biosignal type, a heart sound signal biosignal type, an electromagnetic signal associated with a human body biosignal type, a signal associated with a movement of chest or abdominal muscles biosignal type, and a conductive signal of the human body biosignal type.

The extracting of the physiological features may include extracting, for each of the biosignals, a first same physiological feature type from among a heartbeat physiological feature type, a respiration physiological feature type, a blood pressure physiological feature type, and a body temperature physiological feature type.

The method may further include extracting an other same physiological feature from each of the biosignals, including extracting, from each of the biosignals, a second same physiological feature type from among the heartbeat physiological feature type, the respiration physiological feature type, the blood pressure physiological feature type, and the body temperature physiological feature type, different from the first same physiological feature type.

The determining of whether the biosignals are generated from the same live body may include calculating a first consistent level representing evaluated consistencies between the extracted physiological features, calculating a second consistent level representing evaluated consistencies between the extracted other physiological features, and determining whether the biosignals are generated from the same living body based on both the first and second consistent levels.

The determining of whether the biosignals are generated from the same live body may include calculating a consistent level representing evaluated consistencies between the extracted physiological features based on properties of the extracted physiological features, and determining whether the biosignals are generated from the same living body based on the consistent level satisfying a preset condition.

The determining of whether the biosignals are generated from the same living body based on the consistent level satisfying the preset condition may include determining whether the consistent level satisfies the preset condition based on at least one of a consistent level between a same first physiological feature extracted from each of the biosignals, collected from a body at a same time, and a consistent level between a same second physiological feature extracted from at least two different types of other biosignals collected from one or more other bodies or collected at different times, where the first physiological feature is different from the second physiological feature.

The calculating of the consistent level may include calculating the consistent level based on an evaluated relationship between a waveform of each of the extracted physiological features and a collection time in which a predetermined physiological event is collected.

The physiological event may correspond to a peak or a valley in at least one of the waveforms, wherein the consistent level may represent a difference or a similarity, and wherein the difference may be a variance of a deviation of the collection time corresponding to the peak or the valley, and the similarity may be a reciprocal of the difference.

The calculating of the consistent level may include calculating the consistent level using a learner trained based on input physiological feature data and a preset consistent level.

The properties of the extracted physiological features may include at least one of a time domain property, a frequency domain property, and a statistical property of the extracted physiological features.

The time domain property may include at least one of a moment at which a predetermined physiological event occurs in the extracted physiological features, a moment at which the physiological event changes, a duration of the physiological event, and a signal waveform of each of the extracted physiological features, and the frequency domain property may include a signal frequency spectrum distribution or a signal frequency of each of the extracted physiological features.

The determining of whether the biosignals are generated from the same living body may include classifying the biosignals using a classifier based on one or more properties of the extracted physiological features, the classifier using a first type of samples acquired from first biosignals collected at a same time from a same body and a second type of samples acquired from second biosignals collected from one or more other bodies or collected at different times, and determining whether the biosignals are generated from the same living body based on a result of the classifying.

Classifying of the biosignals may be based on inputting to the classifier the one or more properties of the extracted physiological features, wherein the one or more properties may be at least one of a time domain property, a frequency domain property, and a statistical property of the extracted physiological features.

The time domain property may include at least one of a moment at which a predetermined physiological event occurs in the extracted physiological features, a moment at which the physiological event changes, a duration of the physiological event, and a signal waveform of each of the extracted physiological features, and the frequency domain property may include a signal frequency spectrum distribution or a signal frequency of each of the extracted physiological features.

The extracted physiological features may be physiological features that vary over time for a living body.

The extracted physiological features may include a select one of a heartbeat, a respiration, a blood pressure and a body temperature.

The method may further include performing an authentication or identification of an identity of the living body based on the biosignals being determined to be from the same living body.

The performing the authentication or identification may include determining whether identity feature information extracted from at least one of the biosignals or an other biosignal from the living body matches registered identity feature information, and performing the authentication or identification of the identity of the living body based on a result of the determining of whether the extracted identity feature information matches the registered identity feature information.

The extracted identity feature information may include at least one of a human facial image, a fingerprint image, a palm print image, a blood vessel image, an iris image, a retinal image, an audio signal, a gait feature, a feature of a signature or handwriting, an electrocardiogram (ECG) signal, and an electroencephalogram (EEG) signal.

One or more embodiments include a non-transitory recording medium having processor readable code to control at least one processing device to implement one or more embodiments described herein.

One or more embodiments include a biometric authentication apparatus including a processor configured to extract a same physiological feature from each of at least two different type biosignals and to determine whether the biosignals are generated from a same living body based on a comparison of the extracted physiological features.

The biometric authentication apparatus may further include one or more sensors configured to capture biometric features from a body, the processor being further configured to control a capturing of each of the biosignals at a same time using the one or more sensors.

The processor may be configured to control the one or more sensors to measure the biosignals for a predetermined period of time.

The biometric authentication apparatus may further include a communication device to communicate with one or more remote sensors configured to capture biometric features from a body, the processor being further configured to control or selectively receive a measuring of each of the biosignals, measured at a same time by the one or more sensors.

The biosignals may be each analog or digital information respectively representing a different physical characteristic or behavioral characteristic of a body.

To determine whether the biosignals are generated from the same live body, the processor may be configured to evaluate consistencies between the extracted physiological features and determines whether the biosignals are generated from the same living body based on the evaluated consistencies.

The processor may be configured to extract an other same physiological feature from the biosignals, evaluate consistencies between the extracted other physiological features, and determine whether the biosignals are generated from the same living body based on the evaluated consistencies between the extracted physiological features and the evaluated consistencies between the extracted other physiological features.

The processor may be configured to determine whether identity feature information extracted from at least one of the biosignals or an other biosignal from the living body matches registered identity feature information, and perform an authentication or identification of the identity of the living body based on the determination by the processor of whether the biosignals are generated from the same living body and the determination of whether the extracted identity feature information matches the registered identity feature information.

Other features and aspects will be apparent from the following detailed description, the drawings, and the claims.

Figure 1:
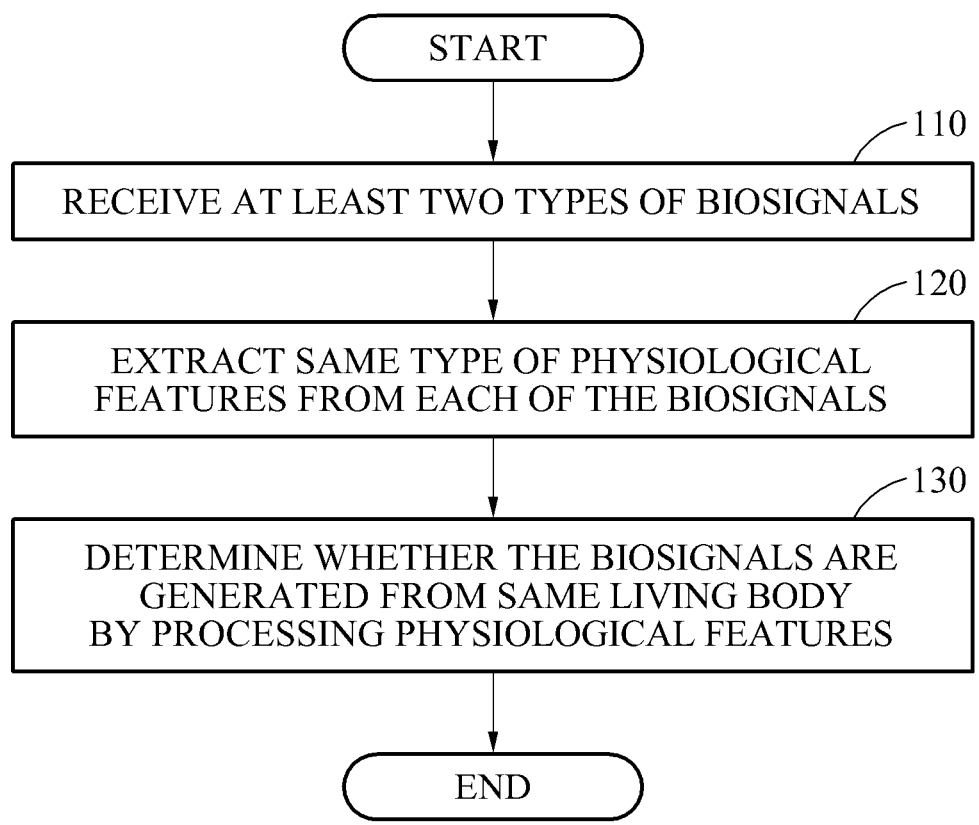
FIG. 1 illustrates a biometric authentication method, according to one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, after an understanding of the present disclosure, various changes, modifications, and equivalents of the methods, apparatuses, and/or systems described herein will be apparent to one of ordinary skill in the art. The sequences of operations described herein are merely examples, and are not limited to those set forth herein, and may be changed as will be apparent to one of ordinary skill in the art, with the exception of operations necessarily occurring in a certain order. In addition, descriptions of functions and constructions that may be well known to one of ordinary skill in the art may be omitted for increased clarity and conciseness.

The features described herein may be embodied in different forms, and are not to be construed as being limited to the examples described herein.

Various alterations and modifications may be made to the embodiments, some of which will be illustrated in detail in the drawings and detailed description. However, it should be understood that these embodiments are not construed as limited to the illustrated forms and include all changes, equivalents, or alternatives within the idea and the technical scope of this disclosure.

Terms used herein are to merely explain specific embodiments, thus are not meant to be limiting. A singular expression includes a plural expression except when two expressions are contextually different from each other. For example, as used herein, the singular forms "a," "an" and "the" are intended to include the plural forms as well, unless the context clearly indicates otherwise. Herein, a term "include" or "have" are also intended to indicate that characteristics, figures, operations, components, or elements disclosed on the specification or combinations thereof exist. The term "include" or "have" should be understood so as not to pre-exclude the existence of one or more other characteristics, figures, operations, components, elements or combinations thereof or additional possibilities.

Unless otherwise defined, all terms including technical and scientific terms used herein have the same meaning as commonly understood by one of ordinary skill in the art to which this invention may belong, in view of the present disclosure. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

Hereinafter, certain embodiments will be explained in more detail with reference to the attached drawings, wherein like reference numerals refer to like elements throughout. Like or the same component or components corresponding to each other will be provided with the same reference numeral, and their repeated detailed explanation may be omitted. In addition, when it is determined that a detailed description of a related or known function or configuration may make a purpose of an embodiment of the present disclosure unnecessarily ambiguous, such a detailed description may be omitted.

FIG. 1 illustrates a biometric authentication method, according to one or more embodiments.

The biometric authentication method of FIG. 1 may be performed by a biometric authentication apparatus, such as by any of the apparatuses of FIGS. 6-14, as only examples. Such biometric authentication apparatuses include a processor and are configured to collect various types of biometric features. Hereinafter, operations of the biometric authentication method will be described. Below, the biometric authentication method of FIG. 1 will be explained with references to such a biometric authentication apparatus as only a convenience for explanation, as embodiments are not limited thereto.

Referring to FIG. 1, in operation 110, the biometric authentication apparatus may receive at least two types of biosignals.

Herein, a biometric feature means a feature that shows a physical characteristic or a behavioral characteristic of a living body. There may be various biometric features that show various characteristics. For example, such biometric features may include a human face, a fingerprint, a palm print, a blood vessel, an iris, a retina, an electrocardiogram (ECG), an electroencephalogram (EEG), a pulse, a blood pressure, a heart sound, a movement of chest or abdominal muscles, or a conductivity of a human body, as only examples.

A biosignal may be any of, e.g., as analog or digital information or data, a human facial image, a fingerprint image, a palm print image, a blood vessel image, an iris image, a retinal image, an ECG signal, an EEG signal, a photoplethysmogram (PPG) signal, a blood pressure signal, a heart sound signal, an electromagnetic signal associated with a human body, a signal associated with a movement of chest or abdominal muscles, a conductive signal of a human body, and other signals representing biometric features, as only example "types" of biosignals. However, the biometric features and biosignals are not limited to those described above, and various biometric features and various biosignals that are currently known or may be developed in the future are available for use by a biometric authentication method or apparatus herein based on an understanding of one or more embodiments discussed herein. In addition, herein, each of the above noted different example biosignals represent different example "types" of biosignals. For example, two biosignals of a same "type" could be a first human facial image and a second human facial image, or a first fingerprint image and a second fingerprint image, etc., while two biosignals of a different "type" could be a human facial image and a fingerprint image, an iris image and a retinal image, a human facial image and an EEG signal, etc.

The biosignals may be collected in various forms, for example, an electronic signal, a sound signal, a force signal, an electromagnetic signal, an image signal, a moving image signal, or an optical signal, for example. In addition, various sensors may be used to collect such biosignals.

For example, a color image sensor may be used to collect a human facial image, a fingerprint image, a palm print image, or a retinal image. In another example, an infrared image sensor may be used to collect an image of a biometric feature sensitive to an infrared light source (for example, a blood vessel image). In still another example, a vibration sensor may be used to collect a signal having a vibration characteristic (for example, a signal associated with a movement of chest or abdominal muscles). In yet another example, a pressure sensor may be used to collect a biosignal associated with a pressure (for example, a blood pressure signal, or a signal associated with a movement of chest or abdominal muscles). Depending on embodiment, various types of biosignals may be simultaneously collected using a plurality of different sensors, respectively, or using an integrated sensor configured to collect various types of biosignals. For example, a color image sensor and a photoelectric sensor may simultaneously collect a human facial image and a PPG signal, respectively, or a sensor having both a capability of the color image sensor and a capability of the photoelectric sensor may simultaneously collect the human facial image and the PPG signal.

Still further, herein, physiological features mean features of physiological states of a living body. Respective physiological features may include a heartbeat, a respiration rate, a blood pressure, or a body temperature, as only example "types" of physiological features. In addition, herein, two physiological features of a same "type" could be a first heartbeat and a second heartbeat, or a first respiration rate and a second respiration rate, a first blood pressure and a second blood pressure, or a first body temperature and a second body temperature, etc., while two physiological features of a different "type" could be a heartbeat and a respiration rate, a heart rate and a blood pressure, a respiration rate and a body temperature, etc.

To acquire a plurality of distributed data points of biometric features that correlate with each other in time and a continuous or sequenced biosignal based on a change in time, various types of biosignals may be collected for respective predetermined same or overlapping periods of time. For example, an ECG signal waveform may be collected for 1 minute, and several human facial images may be collected for 10 seconds of that 1 minute. The collected biosignals may be processed using a signal conversion circuit and the processed signals forwarded to the processor when the signal conversion circuit is part of the biometric authentication apparatus, or transmitted to the processor through a communication channel when the signal conversion circuit is remote relative to the biometric authentication apparatus, such as when the signal conversion circuit is included or connected to a remote sensor that captures a biosignal. In an example, the signal conversion circuit may convert a continuous analogue signal (for example, an ECG signal or a PPG signal) into a digital signal, processes noise included in a signal, and processes an intensity, a distribution, or a change of a signal. For example, the biometric authentication apparatus may remove noise of an image representing an eyelid or an eyebrow from a collected iris image, and may normalize a palm print image.

In operation 120, the processor of the biometric authentication apparatus may extract the same type of physiological features from each of the biosignals.

As noted above, herein, the physiological features refer to features of physiological states of a living body, and may include a heartbeat, a respiration, a blood pressure, or a body temperature, as only examples. For a living body the physiological features typically vary over time. Thus, based on an expectation that the physiological features vary over time, the biometric authentication method may prevent or reject a passing or success of the biometric authentication process based on a false, or potentially false, biosignal that does not correspondingly vary over time. For example, when the biosignals are received in operation 110, the processor of the biometric authentication apparatus may extract the same type of physiological features from each of the received biosignals. In addition, the biometric authentication method may include simultaneously extracting multiple types of physiological features, such as both a heartbeat from each of the biosignals and a respiration rate from each of the biosignals.

The biometric authentication method may include extracting the physiological features using various schemes. Based on a direct corresponding relationship between the biosignals and the physiological features, the biometric authentication apparatus may acquire the physiological features from the biosignals. For example, due to a known relatively stable proportional relationship between a respiratory rate and a pulse rate of a human body (for example, a ratio of 1:4 between a person's respiratory rate and pulse rate), the biometric authentication apparatus may estimate the respiratory rate from a PPG signal. Thus, based on differing corresponding known relationships between the physiological features and characteristics of the biosignals changing during predetermined periods of time, the biometric authentication apparatus may acquire the same type of physiological features from different types of biosignals. For example, a heartbeat may directly correspond to a change in color of a capillary in a human face skin, while a heartbeat may also be captured directly by a heart rate sensor. Therefore, the biometric authentication apparatus may analyze a varying of skin color over time in various human facial images collected in a chronological order during a predetermined period of time, and acquire or estimate a heartbeat from the analyzed variation in skin color.

The extracted physiological features may be represented in various forms. The physiological features may be represented in the form of a vector, a vector set, or a signal waveform, as only examples. For example, when each of the extracted physiological features is represented as a vector, each of the elements of each vector may correspond to a collection time of respective single signal, and a value of each of the elements may indicate an intensity of the corresponding physiological feature, a position, a moment at which the corresponding physiological feature is generated or changes, or other states of the corresponding physiological feature.

As an example of a physiological feature being represented in the form of a vector, a heartbeat may be represented as a single one-dimensional (1D) vector $\tilde{A}=(a_1, a_2, \ldots, a_N)$. In the 1D vector $\tilde{A}=(a_1, a_2, \ldots, a_N)$, N denotes a quantity of samples to be extracted and is equal to or greater than 1. In addition, an element $a_1$ may correspond to a first sample extraction timing and a size or magnitude of the element $a_1$ may correspond to an intensity of a corresponding ECG signal at the first sample extraction timing. Also, an element $a_N$ may correspond to an N-th sample extraction timing and a size or magnitude of the element $a_N$ may correspond to an intensity of the corresponding ECG signal at the N-th sample extraction timing. Furthermore, each of the elements of such a vector may correspond to a moment at which a single physiological feature is generated or changes. In the 1D vector $\tilde{A}=(a_1, a_2, \ldots, a_N)$ representing the heartbeat, for example, the element $a_1$ may indicate a point in time at which a first peak occurs, and the element $a_N$ may indicate a point in time at which an N-th peak occurs.

As an example of a physiological feature being represented in the form of a vector set, each of plural vectors included in the vector set may respectively correspond to a moment at which a single physiological feature is generated or changes, and a degree of a change in that physiological feature. For example, a heartbeat may be represented as a vector set $\alpha=(\tilde{A}_1, \tilde{A}_2, \ldots, \tilde{A}_M)$ (M≥1). In this example, in a first vector $\tilde{A}_1=(a_{11}, a_{12})$, an element au may correspond to a moment at which a first peak occurs, and an element $a_{12}$ may correspond to an intensity of a corresponding ECG signal of the first peak. In addition, an element $a_{M1}$ may correspond to a moment at which an M-th peak occurs, and an element $a_{M2}$ may correspond to an intensity of the corresponding ECG signal of the M-th peak.

In still another example, a physiological feature may be represented in the form of a continuous signal waveform in a two-dimensional (2D) coordinate system. For example, a waveform changing trend may correspond to a changing trend of an intensity of a physiological feature.

Returning to FIG. 1, in operation 130, the processor of the biometric authentication apparatus may determine whether the biosignals are generated from a single same living body by processing the extracted physiological features.

The processor of the biometric authentication apparatus may determine whether the biosignals are generated from the same living body based on a determined or expected difference between representations of physiological features extracted from at least two types of biosignals collected at the same or overlapping times, or simultaneously, from a same living body and representations of physiological features extracted from the at least two types of biosignals collected from different living bodies or collected at different times. The physiological features extracted from the biosignals from the same living body may be represented by, for example, data in the form of a vector. The determined or expected difference may be, for example, a distinguishable difference between a consistent level between the same type of physiological features extracted from the at least two types of biosignals collected from the same living body and a consistent level between the same type of physiological features extracted from the at least two types of biosignals collected from the different living bodies or collected at the different times.

For example, atrial beat frequencies acquired based on facial images collected from the same person in different times (for example, a moment of a relaxed state or a tension state) may relatively greatly differ from each other. Also, heartbeat frequencies acquired based on facial images of different persons may relatively greatly differ from each other. Thus, as described above, the biometric authentication apparatus may determine whether the biosignals are generated from the same living body based on a difference between the physiological features of the example two types of biosignals. In response to a found great difference between the physiological features, the biometric authentication apparatus may determine that collected biosignals are falsely generated or are imitated or copied, e.g., instead of determining that the collected biosignals are generated from the same living body.

To perform an authentication or identification of a living body, the biometric authentication apparatus may perform a biometric detection on a person subject to the authentication or identification based on physiological features. For example, when a consistent level between the same type of physiological features included in at least two types of biosignals collected by one or more sensors satisfies a preset condition, the biometric authentication apparatus may confirm that the person is a real living body.

The processor of the biometric authentication apparatus may process the physiological features extracted from the biosignal. The processing may include, for example, a form conversion, a feature analysis, or a similarity analysis.

In an example, when at least two types of extracted biosignals have different representation forms, the processor of the biometric authentication apparatus may convert the extracted biosignals into signals having the same representation form, which may make comparisons between the extracted biosignals easier. For example, both a heartbeat that is extracted from a PPG signal and that is represented as a vector set, and a heartbeat that is extracted from a human facial image and that is represented as a signal waveform may be converted into respective heartbeats represented as 1D vectors. In this example, the biometric authentication apparatus may determine whether the biosignals are generated from a same living body based on physiological features converted into data in the same form or format.

In another example, the processor of the biometric authentication apparatus may analyze the extracted physiological features. When at least two types of extracted biosignals are represented as a vector set, as described above, the processor of the biometric authentication apparatus may convert the vector set into a matrix, and may calculate a covariance matrix or a feature value of the matrix, to analyze the extracted physiological features.

In still another example, the processor of the biometric authentication apparatus may analyze a similarity or a difference between physiological features included in at least two types of extracted biosignals. As only examples, some schemes for analyzing the similarity or difference will be further described below.

The processor of the biometric authentication apparatus may determine whether at least two types of extracted biosignals are generated from a same living body based on physiological features in the extracted biosignals. For example, when extracted physiological features have the same, or substantially the same, intensity and frequency or show the same, or substantially the same, changing trend, the processor of the biometric authentication apparatus may determine that the biosignals are generated from the same living body.

The processor of the biometric authentication apparatus may obtain or receive at least two types of biosignals, extract a same type of physiological features from each of the biosignals, and determine whether the biosignals are generated from a same living body by processing the extracted physiological features. Thus, the biometric authentication apparatus may significantly increase the difficulty of an illegal use of biometric features, e.g., by preventing use of various biometric features copied from different living bodies or copied in different times, and may enhance stability of an identity authentication by determining whether a living body subject to an authentication or identification process is a real living body.

Figure 2:
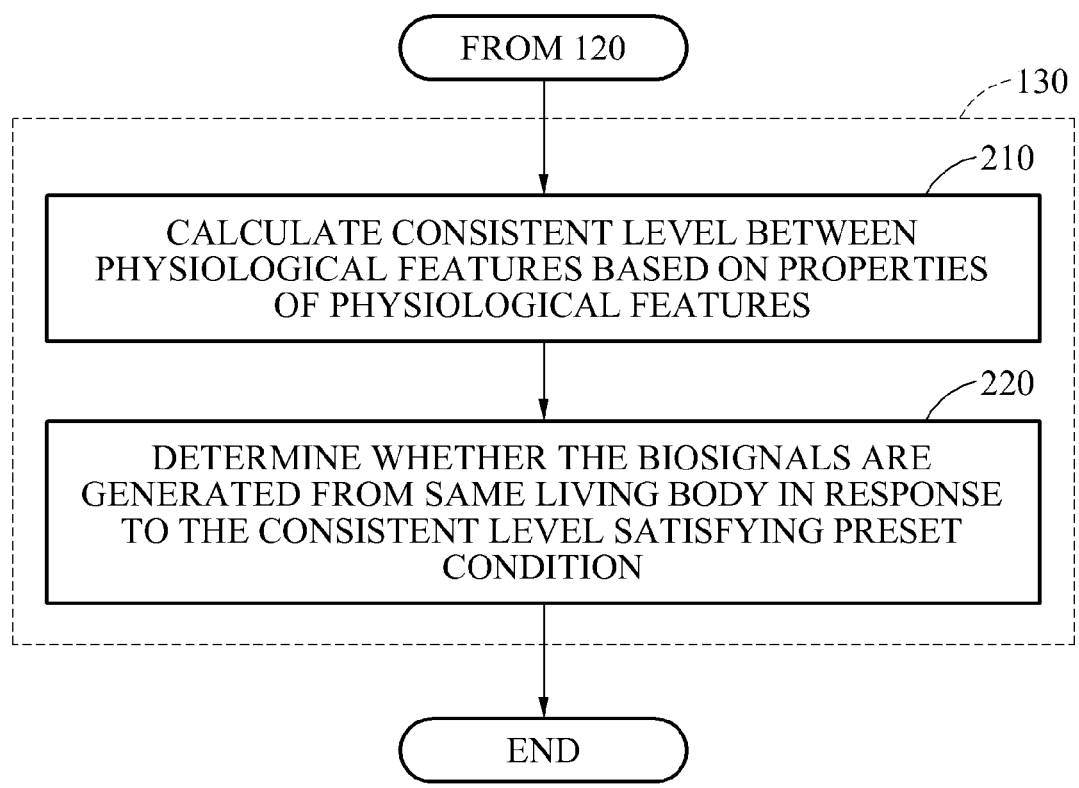
FIG. 2 illustrates a method of determining whether at least two types of biosignals are generated from a same real living body, according to one or more embodiments.

FIG. 2 illustrates a method of determining whether at least two types of biosignals are generated from the same real living body, such as the operation 130 of FIG. 1, as only an example, according to one or more embodiments. Below, the method of FIG. 2 will be explained with references to such a biometric authentication apparatus that may implement the method of FIG. 2 as only a convenience for explanation, as embodiments are not limited thereto.

Thus, a biometric authentication apparatus may determine, for example, whether at least two types of extracted biosignals are generated from a real living body or whether the biosignals are generated from the same living body, through an analysis of a similarity or difference between physiological features included in, or represented by, the biosignals.

Referring to FIG. 2, in operation 210, the processor of the biometric authentication apparatus may calculate a consistent level between the physiological features extracted from the biosignals, based on properties of the physiological features.

Herein, the consistent level means an index of a consistency between at least two types of physiological features, and may be calculated using various schemes. The consistent level may be, for example, a similarity or a difference. For example, when the extracted physiological features are represented in the form of signal waveforms, the processor of the biometric authentication apparatus may calculate a consistent level based on a corresponding relationship between a signal waveform of each of the physiological features and a collection time in which a predetermined physiological event is collected. In this example, the physiological event may correspond to, for example, a peak or a valley in the waveform. The processor of the biometric authentication apparatus may detect a peak moment or a valley moment from a signal waveform of each of physiological features extracted from at least two types of biosignals, to acquire a corresponding relationship between the signal waveform and a collection time of the peak moment or a corresponding relationship between the signal waveform and a collection time of the valley moment.

In an example, when the consistent level is a difference, the difference may be calculated as a variance of a deviation of a collection time corresponding to a peak or a valley in a waveform representing a physiological feature, for example. In another example, when the consistent level is a similarity, the similarity may be calculated as a reciprocal of the difference.

In an example, when two types of biosignals are collected at the same or overlapping times, or simultaneously, from a same living body, a deviation corresponding to a peak moment or a valley moment may be basically constant, and may remain unchanged based on a change in time. In this example, a variance and a difference may be relatively low, whereas a similarity and a consistent level would be relatively high. In another example, when two types of biosignals are collected from different living bodies or collected at different times, a deviation corresponding to a peak moment or a valley moment is unstable, and greatly changes based on a change in time. In this example, a variance and a difference are relatively high, whereas a similarity and a consistent level are relatively low.

Furthermore, the consistent level may be calculated using a scheme of machine learning. For example, the processor of the biometric authentication apparatus may calculate the consistent level using a regression machine. The regression machine is a learner of machine learning using a regression analysis. The regression analysis is performed to output a predetermined value in response to a given input. The learner may be trained on a function inferred from training data through supervised learning.

A learning apparatus configured to train the biometric authentication apparatus may train the regression machine of, or for, the biometric authentication apparatus using input physiological feature data and a preset consistent level. The learning apparatus may generate a single regression machine of, or for, the biometric authentication apparatus by training the regression machine using, as a sample set, data of physiological features artificially generated or collected and an artificially set consistent level.

In an example, during the training of the regression machine, the learning apparatus may set a relatively high consistent level to data of physiological features extracted from biosignals collected at the same or overlapping times, or simultaneously, from a same living body.

In another example, the learning apparatus may train the regression machine by setting a relatively low consistent level between physiological features extracted from biosignals collected from different living bodies or at different times.

When the learning apparatus trains the regression machine, for example, the biometric authentication apparatus may sample a data point with a fixed length from signal waveforms or vectors representing physiological features extracted from different biosignals. Accordingly, when the biometric authentication apparatus transfers such sampled data point to the regression machine, the regression machine may output the corresponding consistent level. Here, as an example, the processor of the biometric authentication apparatus may include the regression machine.

The biometric authentication apparatus may calculate the consistent level based on at least one of a time domain property, a frequency domain property, and a statistical property of each of the physiological features, for example.

The time domain property may include, for example, a moment at which a predetermined physiological event occurs in a physiological feature, a moment at which the physiological event changes, a duration of the physiological event, or a signal waveform representing the physiological feature. The moment which the predetermined physiological event occurs includes, for example, a peak moment or a valley moment in an ECG. The frequency domain property may include, for example, a signal frequency spectrum or a signal frequency of a physiological feature. The statistical property may include, for example, a statistical value of at least one of the time domain property and the frequency domain property. However, properties of physiological features are not limited to those described above, and each of the physiological features may have other properties. The statistical property may be a statistical value of all properties, and may include, for example, an average, a median value, a variance, a deviation or a histogram.

In operation 220, the biometric authentication apparatus may determine whether the biosignals are generated from a same living body in response to a determination of whether the determined consistent level satisfies a preset condition.

Thus, the biometric authentication apparatus may determine, based on the consistent level, whether the biosignals are generated from the same living body. Typically, a consistent level between physiological features of a same living body at the same moment would be relatively high, and a consistent level between physiological features collected from different living bodies or collected in different moments would be relatively low. As described above, the consistent level may be calculated as a similarity or a difference.

The biometric authentication apparatus may determine whether the calculated consistent level satisfies the condition based on at least one of a consistent level between a same type of first physiological features extracted from at least two types of biosignals collected at the same or overlapping times, or simultaneously, from a same living body and a consistent level between a same type of second physiological features extracted from the at least two types of biosignals collected from different living bodies or collected in different times.

For example, a threshold may be set to be a reference value of a consistent level between physiological features of a same living body at the same moment. In an example, when the consistent level calculated in operation 210 is determined to satisfy the condition, for example, when a similarity meets a first preset threshold, e.g., exceeds a first preset threshold, or a difference does not meet a second preset threshold, e.g., is less than the second preset threshold, the biometric authentication apparatus may determine that the two biosignals including the above-described physiological features are generated from the same living body. In another example, when the consistent level calculated in operation 210 is determined to not satisfy the condition, the biometric authentication apparatus may determine that the biosignals including the above-described physiological features are generated from different living bodies or collected at different moments. Accordingly, as described above, when at least one of a plurality of biosignals is a false signal that is forged or copied, or at least the biometric authentication apparatus cannot confirm that the plurality of biosignals come from the same living body, the biometric authentication apparatus may prevent an unauthorized person from passing a biometric authentication process using the forged or copied, or potentially forged or copied, signal.

The threshold may be set based on a result of training the aforementioned regression machine on a predetermined quantity of sample sets, however, there is no limitation thereto. For example, the threshold may be manually set based on a user's experience. An example process by which the biometric authentication apparatus sets such a threshold based on a result obtained by the learning apparatus training the regression machine on the sample sets will be further described below.

The biometric authentication apparatus may select a sample set of consistent levels between physiological features of a same living body, and a sample set of consistent levels between physiological features collected from different living bodies or collected at different times. The biometric authentication apparatus may select a plurality of consistent levels within a predetermined range of the selected sample sets. The biometric authentication apparatus may further calculate, from each of the selected consistent levels, a distribution density or a distribution quantity of the consistent levels between the physiological features of the example same living body, and a distribution density or a distribution quantity of the consistent levels between the physiological features collected from different living bodies or collected at different times. The biometric authentication apparatus may acquire a distribution curve of the consistent levels between the physiological features of the example same living body, and a distribution curve of the consistent levels between the physiological features collected from different living bodies or collected at different times, based on the calculated distribution densities or the calculated distribution quantities. The biometric authentication apparatus may select a consistent level corresponding to an intersecting point where the two distribution curves intersect each other, and determine the selected consistent level as the preset threshold. When the two distribution curves do not intersect, the biometric authentication apparatus may select a single value between a minimum consistent level between the physiological features of the example same living body and a maximum consistent level between the physiological features collected from different living bodies or collected at different times, and determine the selected value as the preset threshold.

Figure 3:
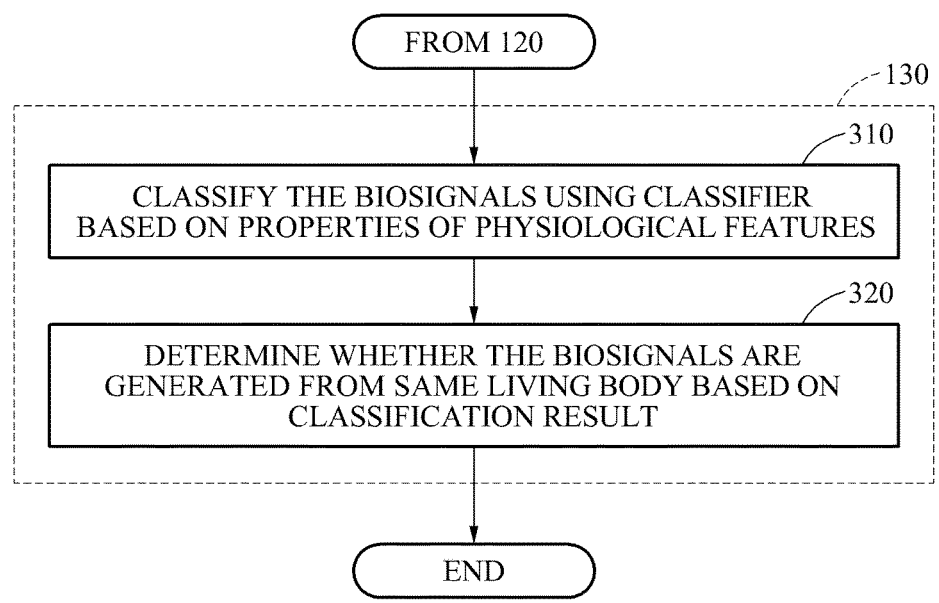
FIG. 3 illustrates a method of determining whether at least two types of biosignals are generated from a same real living body, according to one or more embodiments.

FIG. 3 illustrates a method of determining whether at least two types of biosignals are generated from the same real living body, such as the operation 130 of FIG. 1, as only an example, according to one or more embodiments. Below, the method of FIG. 3 will be explained with references to a biometric authentication apparatus that may implement the method of FIG. 3 as only a convenience for explanation, as embodiments are not limited thereto.

Referring to FIG. 3, in operation 310, a biometric authentication apparatus may classify the biosignals using a classifier based on properties of the extracted physiological features.

The processor of the biometric authentication apparatus may classify at least two types of biosignals using the classifier. The classifier uses two types of samples acquired for training. A first type of samples are acquired from biosignals collected at the same or overlapping times, or simultaneously, from a same living body, and a second type of samples are acquired from biosignals collected from different living bodies or collected at different times. A size of each of the samples may be determined, for example, based on an desired accuracy of a training result and a training time. The biometric authentication apparatus may input, to the classifier, a processed property of a biometric feature (for example, a normalized time domain property, or a normalized frequency domain property). The classifier may use, for example, a support vector machine (SVM) algorithm. To enhance an accuracy of the classifier, the biometric authentication apparatus may classify the biosignals using a strong classifier formed using a cascade of a weak classifier.

The properties include at least one of a time domain property, a frequency domain property, and a statistical property, for example. The time domain property, the frequency domain property, and the statistical property have been already described above regarding FIG. 2 and, accordingly, further description thereof is not repeated here.

In operation 320, the biometric authentication apparatus may determine whether the biosignals are generated from a same living body based on a classification result.

In an example, when a classification result output from the classifier is the same type as the first type of samples used for training, the processor may determine that the biosignals are generated from a same living body. In another example, when the classification result is a different type from the first type of samples, the processor may determine that the biosignals are collected from different living bodies or collected at different times.

Figure 4:
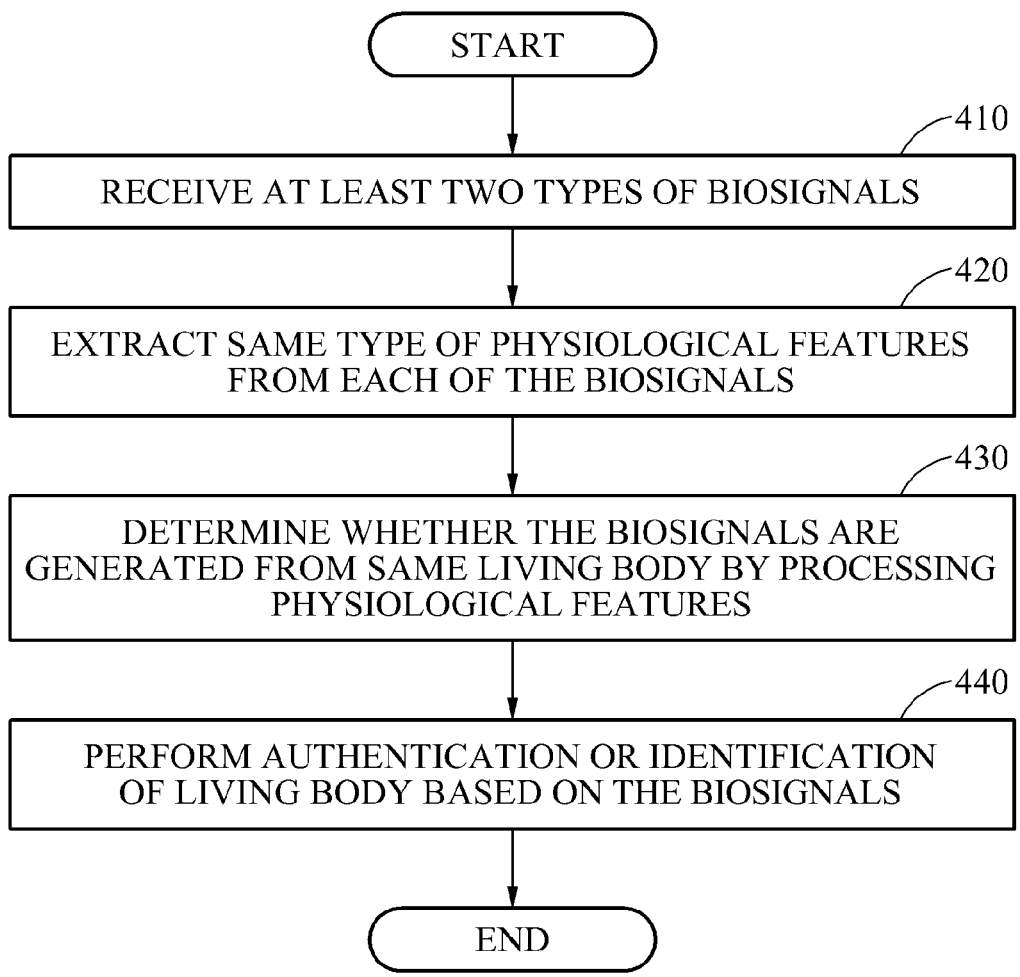
FIG. 4 illustrates a biometric authentication method, according to one or more embodiments.

FIG. 4 illustrates a biometric authentication method, according to one or more embodiments. Below, the biometric authentication method of FIG. 4 will be explained with references to a biometric authentication apparatus that may implement the biometric authentication method as only a convenience for explanation, as embodiments are not limited thereto.

Referring to FIG. 4, in operation 410, a biometric authentication apparatus may obtain or receive at least two types of biosignals.

A processor of the biometric authentication apparatus may obtain or receive the biosignals from one or more sensors. For example, the biosignals may be acquired at the same or overlapping times, or simultaneously, using a plurality of sensors through an optical imaging scheme or a signal detection scheme, however, there is no limitation thereto.

For example, such biosignals may be acquired at the same or overlapping times, or simultaneously, using an integrated sensor that has various sensing or collecting capabilities that use various signal acquisition schemes.

In operation 420, the biometric authentication apparatus may extract the same type of physiological features from each of the biosignals.

The biometric authentication apparatus may extract the same type of physiological features from each of the biosignals, and analyze and acquire a relationship between the biosignals and the physiological features based on a known correlation between the biosignals and the physiological features. The correlation may be, for example, a known direct corresponding relationship between a heartbeat frequency corresponding to a physiological feature and a change in a skin color corresponding to a biosignal. The biometric authentication apparatus may extract the physiological features from each of the biosignals based on a known corresponding relationship between the biosignals and the physiological features. The extracted physiological features may be represented in various forms, such as a vector, a vector set, or a signal waveform, as only examples.

In operation 430, the biometric authentication apparatus may determine whether the biosignals are generated from a same living body, by processing the physiological features.

When the physiological features are extracted, the biometric authentication apparatus may process the physiological features, and determine whether the biosignals are generated from a same living body. For example, the biometric authentication apparatus may convert a form of each of the physiological features and normalize the physiological features, to determine authenticity of various types of biometric features based on data represented in the same form and standard. In addition, the biometric authentication apparatus may determine whether the biosignals are generated from a same living body based on an analysis of the physiological features and a result of an analysis of a similarity between the physiological features.

Operations 410 through 430 of FIG. 4 may be performed similarly to operations 110 through 130 of FIG. 1 and, accordingly, further description thereof is not repeated herein.

In operation 440, the biometric authentication apparatus may perform an authentication or identification of a living body, e.g., corresponding to the same living body of operation 430, based on the biosignals. For example, the biometric authentication apparatus may perform the authentication or identification of the living body based on the determination of whether the biosignals are generated from the same living body in operation 430, which may indicate that the same biosignals considered in the operation of 440 are of a living body and that those biosignals may either, or both, be used for the authentication or identification of the particular living body that the biosignals represent.

Accordingly, the biometric authentication apparatus may perform an authentication or identification of a person based on a result of operation 430. The biosignals may include feature information used to distinguish a particular living body from other living bodies, and the feature information may include, for example, identity feature information. As only an example, while determining whether the biosignals are generated from a same living body in operation 430, the biometric authentication apparatus may also perform an authentication or identification of a person based on identity feature information extracted from the biosignals. The biometric authentication apparatus may perform the authentication or identification based on each of various types of biosignals, and confirm an identity of a person based on a plurality of authentication results or identification results.

Therefore, compared to operations 110-130 of FIG. 1, where there is a determination of whether biosignals are from a same living body, FIG. 4 sets forth a method of operations 410-430, where there is the determination of whether such biosignals are from a same living body, and operation 440, where the biometric authentication apparatus may perform an authentication and identification of an identity of the determined real living body.

Figure 5:
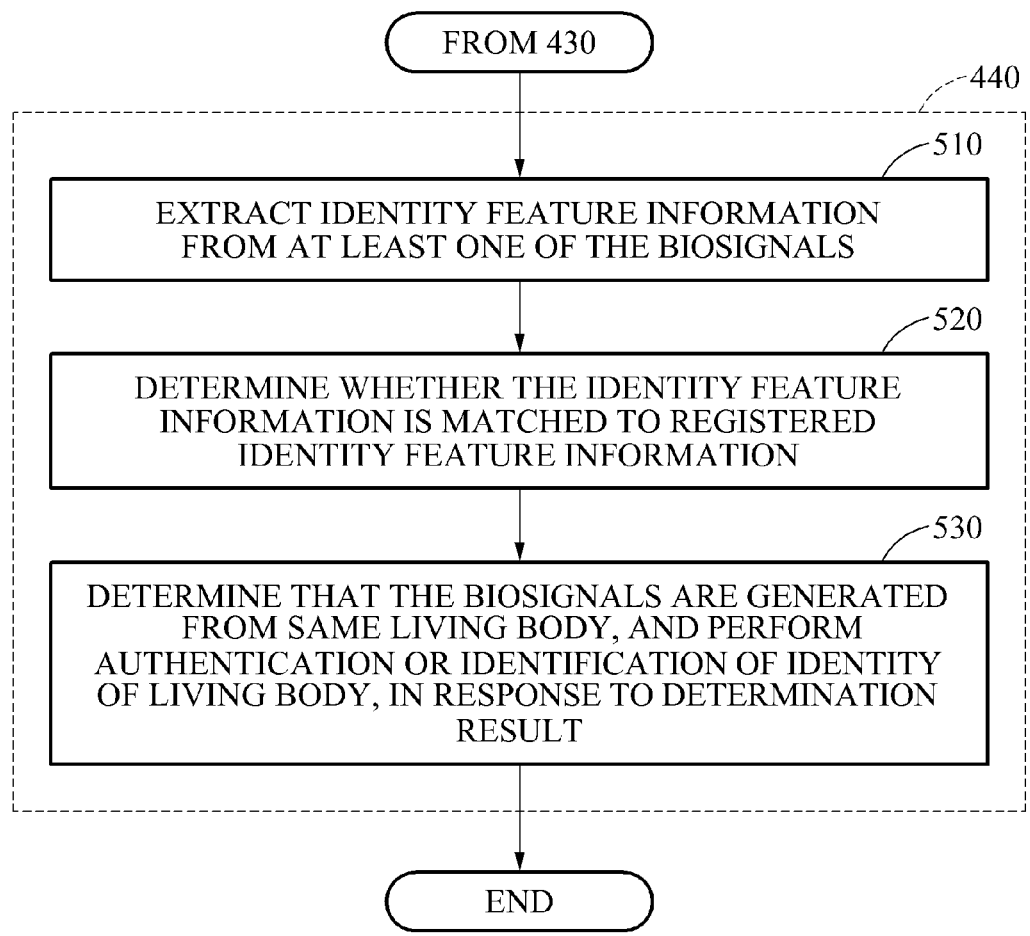
FIG. 5 illustrates an authentication or identification method based on at least two types of biosignals, according to one or more embodiments.

FIG. 5 illustrates an authentication or identification method based on at least two types of biosignals, such as the operation 440 of FIG. 4, as only an example, according to one or more embodiments. Below, the method of FIG. 5 will be explained with references to a biometric authentication apparatus that may implement the authentication or identification method as only a convenience for explanation, as embodiments are not limited thereto.

Referring to FIG. 5, in operation 510, the biometric authentication apparatus may extract identity feature information from at least one of the biosignals.

The identity feature information may be, for example, information that has a relatively high discrimination to be used to discriminate a particular living body from other living bodies. In normal circumstances, a feature indicating uniqueness and stability may be used as identity feature information. As only examples, the identity feature information may include, but is not limited to, a human facial image, a fingerprint image, a palm print image, a blood vessel image, an iris image, a retinal image, an audio signal, a gait feature, a feature of a signature or handwriting, an ECG signal, and an EEG signal. Also, the identity feature information may include currently known identity feature information, and the authentication or identification method is available for identity feature information that may be revealed in the future. To perform an authentication or identification of an identity of a living body, the biometric authentication apparatus may preferentially extract identity feature information of the living body from the biosignals.

The biometric authentication apparatus may use various schemes to extract identity feature information.

In an example, the biometric authentication apparatus may use a directly received biosignal as identity feature information. For example, a human facial image may be used as identity feature information to be used for an identity authentication.

In another example, the biometric authentication apparatus may use a feature extracted from a biosignal as identity feature information. For example, the biometric authentication apparatus may analyze a walking posture and a stride frequency from continuous or sequenced images representing a walking person, and may use a corresponding extracted gait feature as identity feature information.

In still another example, the biometric authentication apparatus may analyze a change pattern of a change in a feature extracted from a biosignal during a predetermined period of time, quantize and represent the change pattern, and use the quantized change pattern as identity feature information. For example, the biometric authentication apparatus may record an ECG signal during a predetermined period of time, quantize a change pattern of a change in a moment at which a peak of the ECG signal occurs, and use the quantized change pattern as identity feature information. The change pattern may be, for example, a peak occurrence interval, or a difference value between a current peak value and a previous peak value every time a peak occurs.

In an example, identity feature information extracted from one type of biosignals among various types of biosignals may be used for authentication or identification. In another example, identity feature information extracted from at least two types of biosignals among the various types of biosignals may be used for authentication or identification. Identity feature information extracted from the various types of biosignals may be of the same type or different types.

Identity feature information may be the same as or different from information on physiological features extracted to determine authenticity of a living body. When the identity feature information is the same as the information on physiological features, the biometric authentication apparatus may directly use the physiological features extracted in operation 420 of FIG. 4, instead of performing operation 510.

In operation 520, the biometric authentication apparatus may determine whether the identity feature information is matched to identity feature information that is registered.

The biometric authentication apparatus may perform two types of pattern matching, for example authentication pattern matching or identification pattern matching, on the extracted identity feature information and identity feature information registered in a database. In an example, to perform the authentication pattern matching, the biometric authentication apparatus may determine whether the extracted identity feature information is matched to identity feature information that is associated with an estimated living body and that is registered in the database. In another example, to perform the identification pattern matching, the biometric authentication apparatus may search for a living body corresponding to identity feature information with a highest matching level with the extracted identity feature information through a traversal and search of the extracted identity feature information and all the identity feature information registered in the database.

Prior to the matching of the identity feature information, the biometric authentication apparatus may perform preprocessing on the extracted identity feature information. In an example of an iris identification, the biometric authentication apparatus may extract an iris area from a collected image of an eye region and may normalize the iris area. The biometric authentication apparatus may remove noise from the normalized iris area or perform emphasizing in the normalized iris area, for example. The biometric authentication apparatus may extract a texture feature of an iris using a filtering scheme, and perform template matching of an iris database. In another example, the biometric authentication apparatus may calculate a similarity between an extracted iris feature vector (for example, a vector representation of an iris feature) and a template vector stored in a database. The similarity may be a Euclidean distance, a Hamming distance, a square deviation, or a correlation coefficient, as only examples.

In operation 530, the biometric authentication apparatus may determine that the biosignals are generated from the same living body, e.g., based on an operation similar to operation 430 in FIG. 4 and/or based on the results of operation 520, and perform an authentication or identification of an identity of the living body.

When the biosignals are determined to be generated from the same living body, the biometric authentication apparatus may permit the authentication or identification of the identity of the living body, and perform the authentication or identification of the identity of the living body based on the determination result.

In an example, to perform authentication pattern matching, in response to the extracted identity feature information being determined to be identical to identity feature information of a target living body in the database, the biometric authentication apparatus may determine a living body corresponding to the extracted identity feature information as a target living body. In response to the extracted identity feature information being different from the identity feature information of the target living bodies in the database, the biometric authentication apparatus may determine that the living body corresponding to the extracted identity feature information is different from the target living bodies in the database.

In another example, as noted above, to perform identification pattern matching, the biometric authentication apparatus may identify, as an identity of a target living body to be identified, an identity corresponding to identity feature information with a highest matching level with identity feature information of the target living body in the database.

Thus, the biometric authentication apparatus may determine whether the biosignals are generated from the same living body based on a determination result of operation 520. For example, if identity feature information was obtained from two biosignals and the respective identity feature information is found to match a same living body in the database, then the biometric authentication apparatus may determine that the biosignals are generated from the same living body. Accordingly, the biometric authentication apparatus may extract a plurality of pieces of identity feature information of the same type or different types in operation 510, determine whether each of the pieces of identity feature information is matched to the registered identity feature information in operation 520, and perform an authentication or identification of an identity of the living body based on a plurality of determination results in operation 530.

Because the biometric authentication apparatus, according to one or more embodiments, may determine a false biosignal, or a potentially false biosignal, and authenticate or identify an identity of only a living body, it is possible to strengthen stability of the authentication of an identity. The biometric authentication apparatus may simultaneously collect at least two types of biosignals during the authentication or identification of the identity. Furthermore, the biometric authentication apparatus may acquire physiological features based on a change in time by collecting signals continued during a preset period of time.

Figure 6:
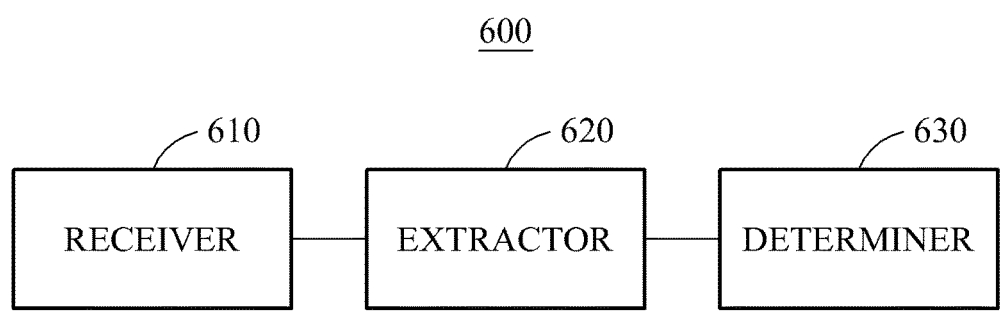
FIGS. 6 and 7 illustrate configurations of biometric authentication apparatuses, according to two or more embodiments.
Figure 7:
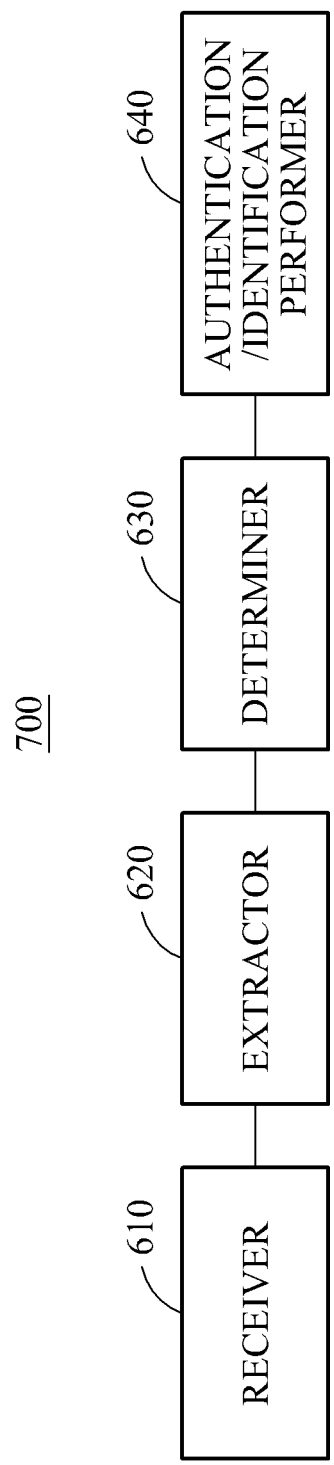

FIGS. 6 and 7 illustrate configurations of a biometric authentication apparatus, according to two or more embodiments.

Referring to FIG. 6, the biometric authentication apparatus 600 may include a receiver 610, an extractor 620, and a determiner 630. The receiver 610 may receive or obtain at least two types of biosignals. The extractor 620 may extract a same type of physiological features from each of the biosignals. The determiner 630 may determine whether the biosignals are generated from a same living body by processing the physiological features.

The receiver 610 receives or obtains the biosignals from one or more sensors. For example, the biosignals may be acquired at the same or overlapping times, or simultaneously, using a plurality of sensors through an optical imaging scheme or a signal detection scheme, as only examples, or using an integrated sensor that has various sensing or collecting capabilities that use various signal acquisition schemes.

The extractor 620 may extract the same type of physiological features for each of the types of biosignals. Due to known correlations between such biosignals and particular physiological features, the extractor 620 may acquire the physiological features by analyzing respective relationships between the biosignals and the physiological features based on the correlations. The correlation may be, for example, an expected direct corresponding relationship between a heartbeat frequency and a change in a skin color. The extractor 620 may extract the physiological features from each of the biosignals based on a corresponding relationship between the biosignals and the physiological features.

The extracted physiological features may be represented in various forms or formats. The physiological features may be represented in a vector, a vector set, or a signal waveform, as only examples.

The determiner 630 may process the above-described physiological features, and determine whether the biosignals are generated from a same living body. The determiner 630 may convert a form of one or more of the physiological features and normalize the physiological features, to determine authenticity of various types of biometric features based on data represented in the same form and standard, for example. The determiner 630 may determine whether the biosignals are generated from a same body based on an analysis of the physiological features and a result of an analysis of similarities between the physiological features.

Also, the determiner 630 may determine whether the biosignals are generated from a same living body, based on a distinguishable difference between consistent level between representations of the same type of physiological features (for example, data represented as a vector) extracted from at least two types of biosignals collected at the same or overlapping times, or simultaneously, from a same living body, and a consistent level between representations of the same type of physiological features extracted from the at least two types of biosignals collected from different living bodies or collected at different times.

In an example, the determiner 630 may calculate a consistent level based on a corresponding relationship between a waveform of each of the physiological features and a collection time in which a predetermined physiological event is collected. The physiological event may correspond to, for example, a peak or a valley in the waveform. The consistent level may be, for example, a difference or a similarity. The difference may be calculated as a variance of a deviation of a collection time corresponding to the peak or the valley, and the similarity may be calculated as a reciprocal of the difference.

In another example, the determiner 630 may calculate a consistent level using a regression machine, e.g., of the determiner 630. A learning apparatus may train the regression machine using input physiological feature data and a preset consistent level. The determiner 630 may also classify the biosignals using a classifier based on properties of the physiological features. The classifier uses two types of samples acquired for training. A first type of samples are acquired from biosignals collected at the same or overlapping times, or simultaneously, from a same living body, and a second type of samples are acquired from biosignals collected from different living bodies or collected at different times. The determiner 630 may determine whether the biosignals are generated from the same living body based on a classification result.

Referring to FIG. 7, a biometric authentication apparatus 700 includes a receiver 610, extractor 620, determiner 630, and an authentication and/or identification (authentication/identification) performer 640. The receiver 610, extractor 620, and determiner 630 may operate the same as discussed above for the biometric authentication apparatus 600 of FIG. 6, and thus the corresponding discussion will not be repeated. The authentication/identification performer 640 may perform an authentication or identification of an identity based on the biosignals. The authentication/identification performer 640 may perform the authentication or identification of the identity based on whether the biosignals are determined as being generated from the same living body. For example, the authentication/identification performer 640 may determine whether the identity feature information extracted from the biosignals is matched to identity feature information that is registered. In response to a result of that determining, the authentication/identification performer 640 may determine that the biosignals are generated from the same living body and perform an authentication or identification of an identity of the living body.

In the biometric authentication apparatuses of FIGS. 6 and 7, the receiver 610, the extractor 620, the determiner 630, and the authentication/identification performer 640 may be implemented by hardware or a combination of hardware and software. The receiver 610, the extractor 620, the determiner 630, and the authentication/identification performer 640 may be a processing device, processor, or specialized computer, for example. For example, the processor may include the receiver 610, the extractor 620, the determiner 630, and the authentication/identification performer 640. The referenced names of the components of the biometric authentication apparatus 600 are not limited to those described above. For example, the receiver 610 may be understood as a "device configured to receive at least two types of biosignals."

The above-described biometric authentication methods are available in an identity authentication system for various types of multiple biometric features. Accordingly, a biometric authentication apparatus is described with reference to FIG. 8 below.

Figure 8:
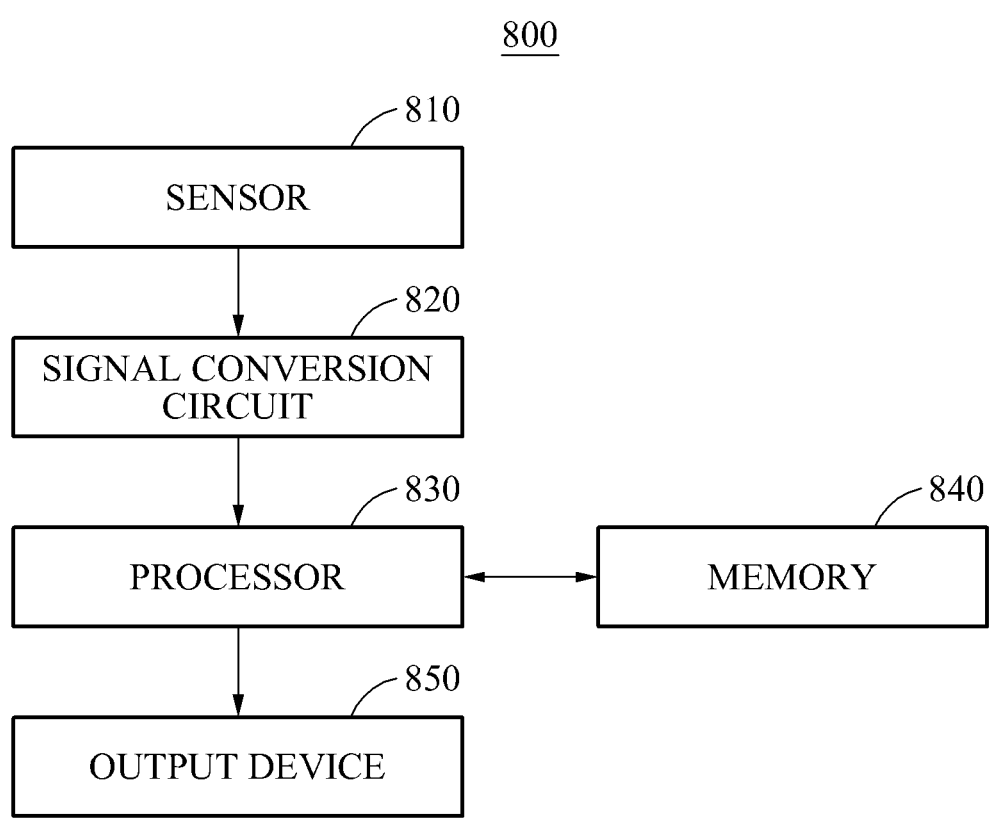
FIG. 8 illustrates a configuration of a biometric authentication apparatus, according to one or more embodiments.

FIG. 8 illustrates a configuration of a biometric authentication apparatus, according to one or more embodiments.

Referring to FIG. 8, the biometric authentication apparatus 800 may include a sensor 810 and a processor 830.

The sensor 810 may collect at the same or overlapping times, or simultaneously, at least two types of biosignals.

The processor 830 may receive or obtain the biosignals from the sensor 810, extract a same type of physiological features from each of the biosignals, process the physiological features, and determine whether the biosignals are generated from a same living body.

The biometric authentication apparatus 800 may further include a signal conversion circuit 820. The sensor 810 may collect the biosignals for a preset period of time, and acquire a distributed data point of a plurality of biometric features that correlate with each other in time and a continuous or sequenced biosignal based on a change in time. The signal conversion circuit 820 may convert the collected biosignals to data capable of being processed in the processor 830, and transmit or forward the data to the processor 830. For example, the signal conversion circuit 820 may convert a continuous analog signal into a digital signal, and may process noise in the digital signal or process an intensity, a distribution, or a change in the digital signal.

In addition, the biometric authentication apparatus 800 may further include a memory 840. The memory 840 may store data, a parameter, or an instruction used during processing of the biosignals, or record a result and data acquired during an operation of the biometric authentication apparatus 800.

Furthermore, the biometric authentication apparatus 800 may further include an output device 850. The output device 850 may output a result acquired through processing by the processor 830. For example, the output device 850 may display explanation for usage, authenticity of a signal, or an identity authentication result or an identity identification result, may operate other equipment, or may run software. As only examples, the output device may unlock use of data or applications of a desktop, laptop, smartphone, portable display, or smartwatch, display ignition information of a vehicle, acknowledge authority to enter a secured area and potentially unlock the passageway to the secured area, or provide personal health or related information to a user through a electronic bracelet or earphone(s), as well as other operations, depending on embodiment.

As noted, the above-described biometric authentication apparatus 800 is applicable to various types of equipment requiring an authentication or identification of an identity. For example, the biometric authentication apparatus 800 may determine whether a subject, i.e., a subject for authentication, is a living body, or may be used to identify a single living body from among a plurality of registrants. Some example biometric authentication apparatuses and corresponding systems that may similarly respectively include such sensor(s) 810, signal conversion circuit(s) 820, processor(s) 830, memories(s) 840, and output device(s) 850 will now be further discussed below with reference to FIGS. 9-14.

FIGS. 9 through 14 illustrate biometric authentication apparatuses, according to example embodiments. Here, though FIGS. 9-14 refer to example embodiments, these embodiments are discussed only as non-limiting examples and are not meant to limit or exclude other implementations derived from the teachings of the present disclosure.

Figure 9:
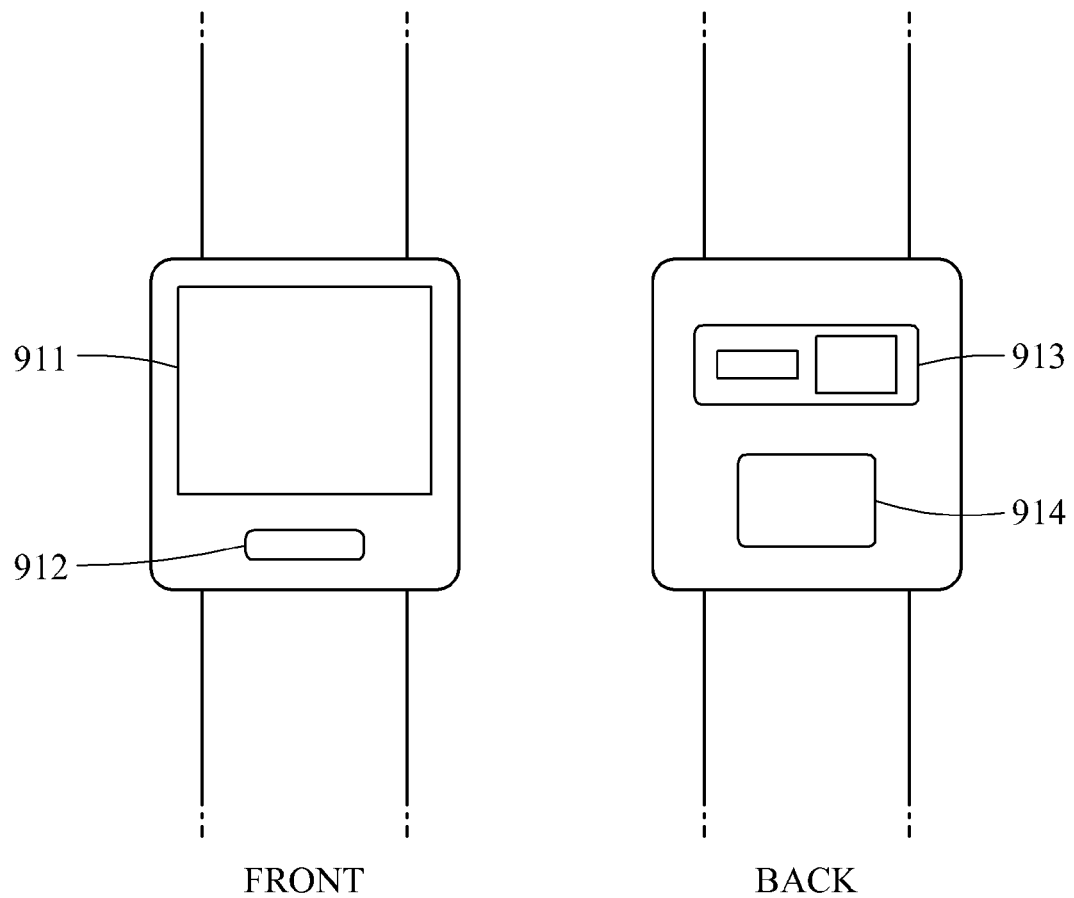
FIGS. 9 through 14 illustrate biometric authentication apparatuses according to example embodiments.

FIG. 9 illustrates a smartwatch 910, configured to implement an identity authentication process based on an ECG signal and a PPG signal, as the biometric authentication apparatus.

Electrodes 912 and 914 of an electrocardiography may be installed as sensors on a front side and a back side of the smartwatch 910, respectively, and used to collect an ECG signal. A PPG sensor 913 may collect a PPG signal. A processor of the smartwatch 910 may receive or obtain the collected ECG signal and the collected PPG signal, extract a heartbeat feature or a respiration feature from the received ECG signal and the received PPG signal, and analyze the heartbeat feature or the respiration feature. Also, the processor may determine whether the ECG signal and the PPG signal are collected from the same user at the same time based on a determined consistent level between the extracted heartbeat feature and the extracted respiration feature, and verify an identity of the user. A screen 911 may display a result of the determining and verifying, as well as display further features of the smartwatch 910 that may become available upon the verification of the identity of the user. Here, the illustrated smartwatch 910 may be an arbitrary smartwatch and the illustrated shape, arrangement, and configuration of the same, as well as the illustrated shape, arrangement, and relative configuration of the smartwatch 910, electrodes 912/914, and PPG sensor 913, are only for example purposes and should not be considered as limiting or excluding other shapes, arrangements, or relative configurations. In addition, in an identity authentication system, one or more of the sensors for the ECG signal and the PPG signal may be separate from the housing of the smartwatch 910 and communicate the collected ECG and/or PPG signals to the processor of the smartwatch 910, for example, through wireless communication to implement the authentication process.

Figure 10:
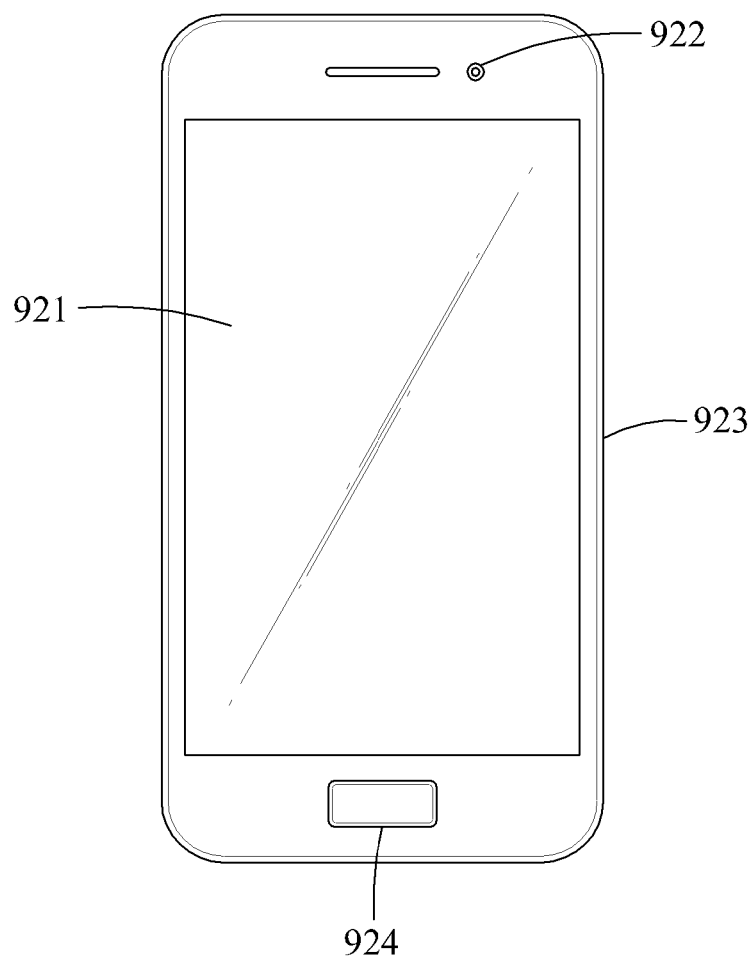

FIG. 10 illustrates a smartphone 920, configured to implement an identity authentication process based on a human facial image and an ECG signal, as the biometric authentication apparatus.

In FIG. 10, a screen 921 may display a collected signal and a processing result. A camera 922 may collect a human facial image. ECG electrodes 923 and 924 may collect ECG signals. A processor of the smartphone 920 may receive or obtain the collected human facial image and the collected ECG signals, and extract a heartbeat feature from the received human facial image and the received ECG signals. The processor may further processes the extracted heartbeat feature, and determine or verify the authenticity of a user's identity based on the processed heartbeat feature. As noted, the screen 921 may display a result of the determining and verifying, as well as display further features of the smartphone 920 that may become available upon the verification of the identity of the user. Here, the illustrated smartphone 920 is an arbitrary smartphone and the illustrated shape, arrangement, and configuration of the same, as well as the illustrated shape, arrangement, and relative configuration of the smartphone 920, screen 921, electrodes 922/924, and camera 922, are only for example purposes and should not be considered as limiting or excluding other shapes, arrangements, or relative configurations.

Figure 11:
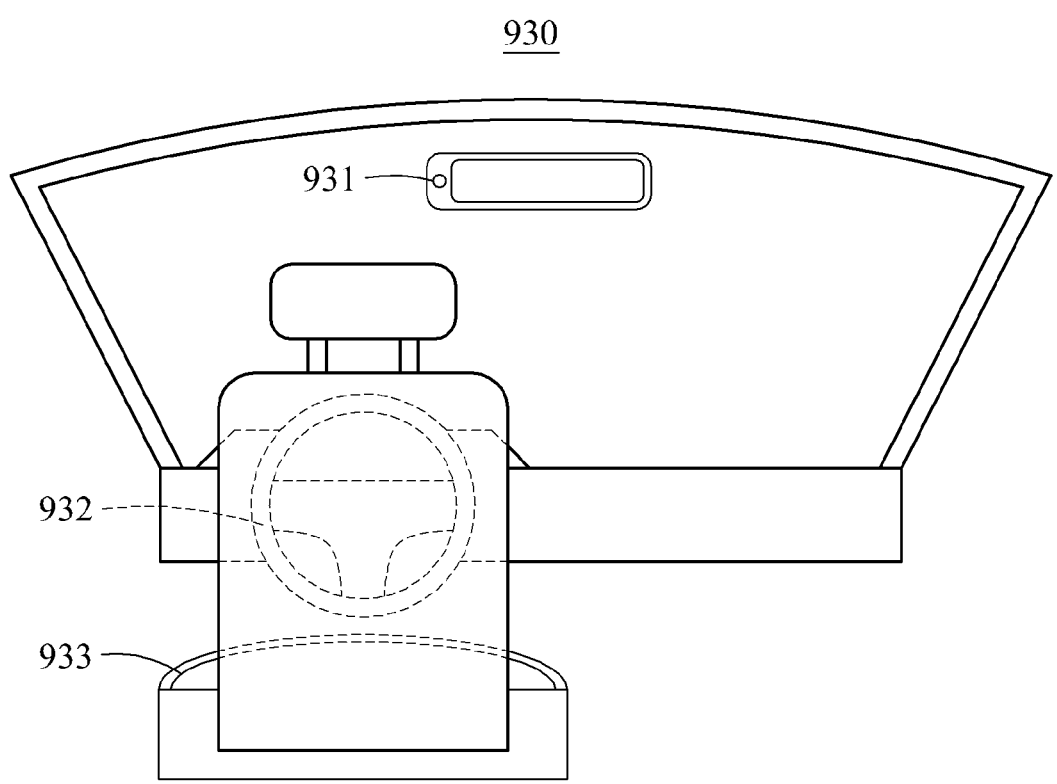

FIG. 11 illustrates a vehicle 930, configured to implement an identity authentication process based on a human facial image, an ECG signal, and a tensile force signal, as the biometric authentication apparatus.

In FIG. 11, a camera 931 may be mounted in a rearview mirror and collect a human facial image, noting that the camera 931 may be arranged or positioned at alternate locations as well. An ECG electrode 932 mounted in a steering wheel, for example, may collect an ECG signal. A tensile force sensor 933 mounted in a seat belt, for example, may collect a tensile force signal. A processor of the vehicle 930 may receive or obtain the collected biosignals, for example, the collected human facial image, the collected ECG signal, and the collected tensile force signal, and extract a heartbeat feature or a respiration feature from each of the biosignals. The processor may further process the extracted heartbeat feature or the extracted respiration feature, determine whether the biosignals are generated from a same living body based on a consistent level between the processed heartbeat feature and the processed respiration feature, and determine or verify the authenticity of a user's identity based on the processed heartbeat or respiration feature and/or human facial image. Here, the vehicle 930 may be an arbitrary vehicle and the illustrated shape, arrangement, seat positioning, and configuration of the same, as well as the illustrated shape, arrangement, and relative configuration of the vehicle 930, ECG electrode 932, sensor 933, and camera 931, are only for example purposes and should not be considered as limiting or excluding other shapes, arrangements, seat positioning, or relative configurations.

Figure 12:
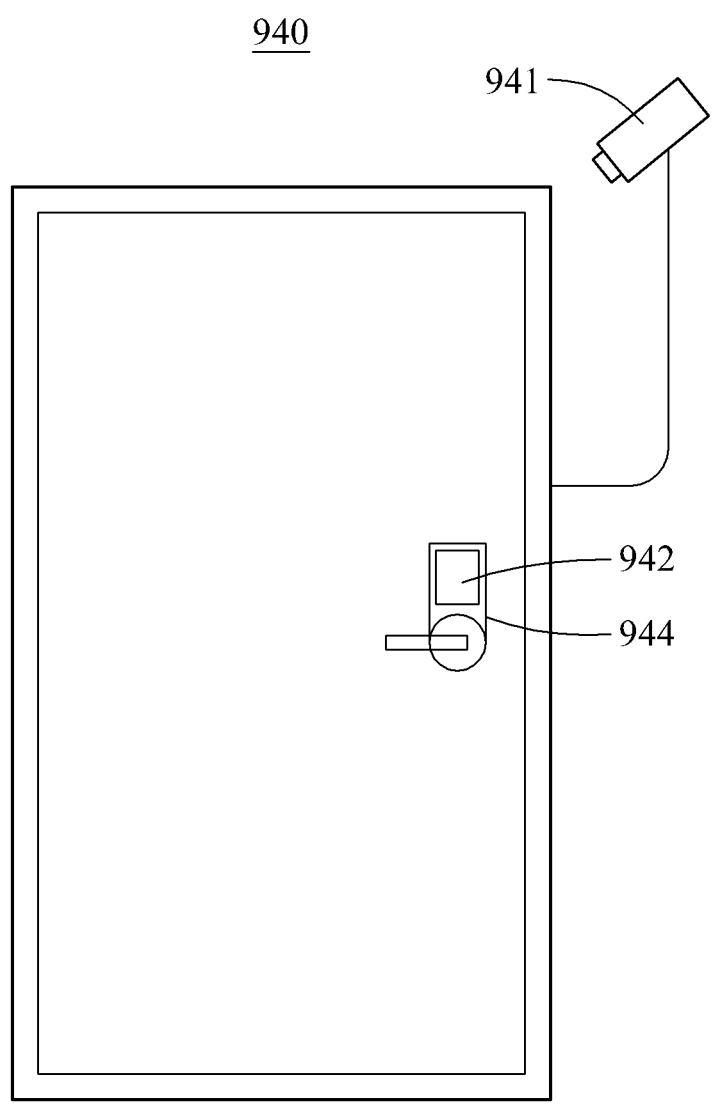

FIG. 12 illustrates a locking system 940 including a biometric authentication apparatus 944 configured to implement an identity authentication process based on a human facial image and a fingerprint image.

In FIG. 12, a camera 941 may be installed above a door and collect a human facial image, a sensor 942 may be installed in a locking device of the door, and collect a fingerprint image, a vein image, or a palm print image, and a processor of the biometric authentication apparatus 944 may determine whether the biosignals are generated from a same living body based on the collected facial image and the fingerprint image, vein image, and/or palm print image, and determine or verify the authenticity of a user's identity or authority to access a secured area behind the door. In an embodiment, the locking device of the door may be part of the biometric authentication apparatus. Here, the illustrated shape, arrangement, and relative configuration of camera 941 and/or sensor 942 of the locking system 940 are only for example purposes and should not be considered as limiting or excluding other shapes, arrangements, or relative configurations. As only an example, the biometric authentication apparatus may be housed in the locking system 940 separate from the sensor 942 and/or the locking device of the door and receive the collected facial image and/or the fingerprint image, vein image, and/or palm print image through a distanced wired or wireless connection or communication channel.

Figure 13:
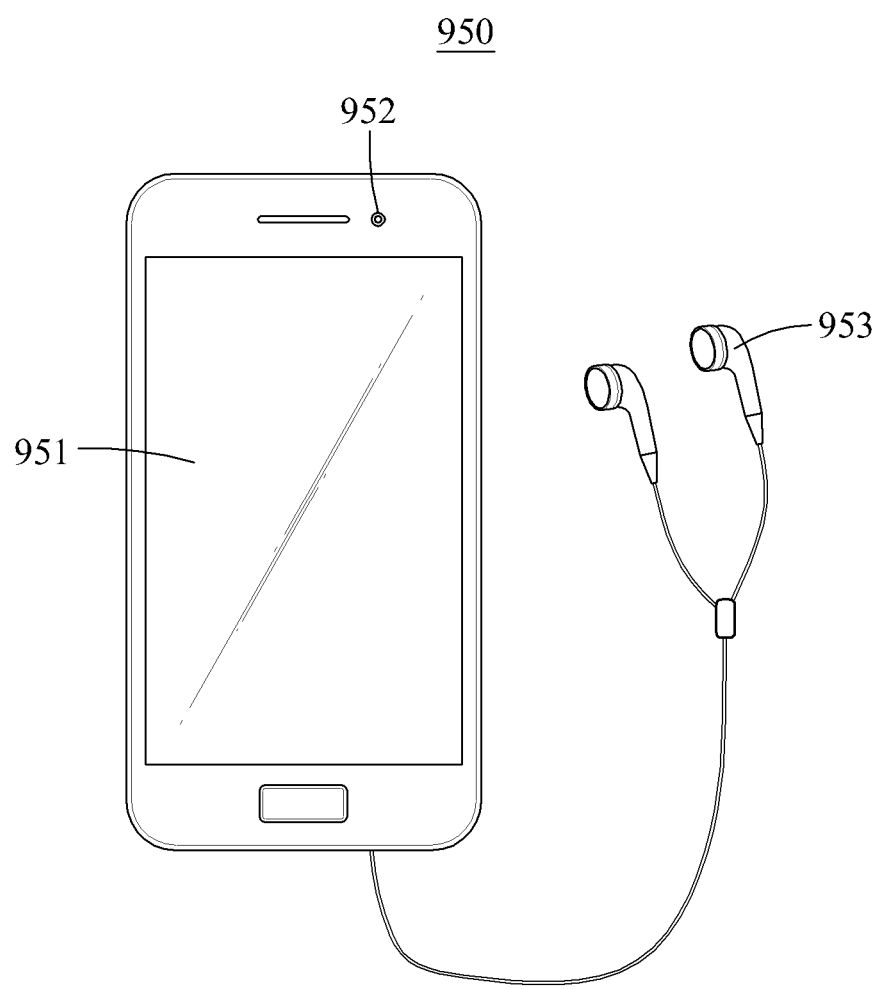

FIG. 13 illustrates a smartphone 950, configured to implement an identity authentication process based on a human facial image and a heartbeat feature, as the biometric authentication apparatus.

In FIG. 13, a camera 952 installed in a front side of the smartphone 950 may collect a human facial image. A pulse sensor 953 may be installed in earphones that are connected to, or in communication with, the smartphone 950. For example, when a user performs an identity authentication, a processor of the smartphone 950 may receive or obtain a human facial image collected from an image sensor of the camera 952, and extract a heartbeat feature from the received human facial image. The pulse sensor 953 may collect a heartbeat feature, and the processor may analyze the two heartbeat features, for example, the heartbeat feature extracted from the human facial image and the heartbeat feature collected by the pulse sensor 953, and determine the authenticity of a living body. A screen 951 may display a collected image and a pulse signal. The screen 951 may display a result of a determining and verifying of the authenticity and identity of the living body, as well as display further features of the smartphone 950 that may become available upon the verification of the identity of the living body. The illustrated smartphone 950 is an arbitrary smartphone and the illustrated shape, arrangement, and configuration of the same, as well as the illustrated shape, arrangement, and relative configuration of the smartphone 950, the camera 952, and pulse sensor 953, are only for example purposes and should not be considered as limiting or excluding other shapes, arrangements, or relative configurations.

Figure 14:
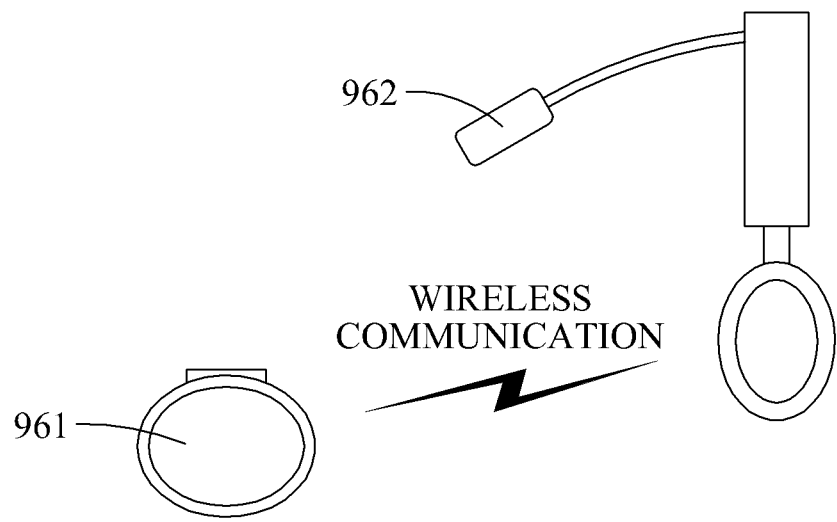

FIG. 14 illustrates a system 960 including an electronic bracelet and earphone(s), where either or both of the electronic bracelet and earphone(s) may be biometric authentication apparatuses that are configured to implement an identity authentication process based on an ECG signal and an EEG signal.

When a user performs an identity authentication, an ECG sensor 961 installed in the electronic bracelet may collect an ECG signal, and an EEG sensor 962 installed in the earphone(s) may collect an EEG signal. Accordingly, during identity biometric authentication operation, a processor of a biometric authentication apparatus may receive or obtain the ECG signal and the EEG signal, and extract a heartbeat feature from each of the ECG signal and the EEG signal. The processor may determine whether the extracted heartbeat feature is collected from a same living body. Furthermore, the processor may verify or identify an identity of the living body. In addition, for example, the processor may combine data, such as additional information based on the extracted heartbeat feature, and transmit the data to either the electronic bracelet or the earphones, for respective display or audio indication, once the identity verification or identification has occurred. For example, when the processor is included in the electronic bracelet, and the electronic bracelet is the biometric authentication apparatus, the electronic bracelet may be configured to display the extracted heartrate feature as a heartrate to the user and/or transmit, e.g., through wireless communication, information of the extracted heartrate feature to the earphone(s) for an audio indication of the heartrate. Alternatively, when the processor is included in the earphone(s), and the earphone(s) is the biometric authentication apparatus, the earphone(s) may be configured to provide the user an audio indication of the heartrate based on the extracted heartrate feature and/or transmit, e.g., through wireless communication, information of the extracted heartrate feature to the electronic bracelet to display the information to the user as a heartrate. Here, the illustrated shape, arrangement, and relative configuration of the ECG sensor 961 and EEG sensor 962, as well as the respective hardware that may include or carry the ECG sensor 961 and EEG sensor 962, are only for example purposes and should not be considered as limiting or excluding other shapes, arrangements, relative configurations, or other hardware placements.

Lastly, as another example, the smartphone of FIG. 13 may be the biometric authentication apparatus and include the processor and both the electronic bracelet and the earphone(s) may act as sensors for the respective ECG and EEG signals, so that the smartphone may extract the heartrate feature, for example, and the smartphone may determine whether the biosignals are of a same living body and accordingly verify or identify the identity of the living body. The smartphone may also transmit information of the extracted heart rate feature back to the electronic bracelet and/or the earphone(s) for respective display or audio indication of the user's heartrate.

With regard to the example embodiments of FIGS. 9-14, it is again noted that these examples are meant to merely be demonstrative of some implementations of aspects of the invention. In addition, embodiments that are demonstrated as being systems where the sensors, any camera, and processor to implement the authentication process may be enclosed or supported by a same housing or enclosure, these systems may alternatively be implemented where any of the sensors and camera may be housed or supported separately from the housing or enclosure that includes the processor and may communicate the sensed biosignals to the processor either through a distanced wired or wireless connection or communication channel. Likewise, embodiments that are demonstrated as being systems where any of the sensors or camera are housed or supported separately from the housing or enclosure of the device that includes the processor to implement the authentication process may alternatively be configured so that any or all of the sensors or camera are housed or supported together by the device that includes the processor. In addition, though a particular number of sensors, a camera, and/or a processor may be discussed in any of the above embodiments, alternative embodiments may include more sensors, cameras, and/or processors for any of the above biometric authentication processes and apparatuses.

In addition, apparatuses, units, modules, devices, and other components illustrated in FIGS. 6-14, for example, that may perform one or more operations described herein with respect to FIGS. 1-5, for example, are implemented by hardware components. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, controllers, sensors, memory, drivers, processing devices, and any other electronic components known to one of ordinary skill in the art. In one example, the hardware components are implemented by one or more processing devices, or processors, or computers. A processing device, processor, or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processing device, processor, or computer includes, or is connected to, one or more memories storing computer readable code, instructions, or software that are executed by the processing device, processor, or computer and that may control the processing device, processor, or computer to implement one or more methods described herein. Hardware components implemented by a processing device, processor, or computer execute code, instructions, or software, such as an operating system (OS) and one or more software applications that run on the OS, to perform the operations described herein with respect to FIGS. 1-5, as only an example. The hardware components also access, manipulate, process, create, and store data in response to execution of the instructions or software. For simplicity, the singular term "processing device", "processor", or "computer" may be used in the description of the examples described herein, but in other examples multiple processing devices, processors, or computers are used, or a processing device, processor, or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, remote processing environments, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-5 that perform the operations described herein may be performed by a processing device, processor, or a computer as described above executing processor or computer readable code, instructions, or software to perform the operations described herein.

Processor or computer readable code, instructions, or software to control a processing device, processor, or computer to implement the hardware components and perform the methods as described above may be written as computer programs, code segments, instructions or any combination thereof, for individually or collectively instructing or configuring the processing device, processor, or computer to operate as a machine or special-purpose computer to perform the operations performed by the hardware components and the methods as described above. In one example, the processor or computer readable code, instructions, or software include machine code that is directly executed by the processing device, processor, or computer, such as machine code produced by a compiler. In another example, the processor or computer readable code, instructions, or software include higher-level code that is executed by the processing device, processor, or computer using an interpreter. Based on the disclosure herein, and after an understanding of the same, programmers of ordinary skill in the art can readily write the processor or computer readable code, instructions, or software based on the block diagrams and the flow charts illustrated in the drawings and the corresponding descriptions in the specification, which disclose algorithms for performing the operations performed by the hardware components and the methods as described above.

The processor or computer readable code, instructions, or software to control a processing device, processor, or computer to implement the hardware components, such as discussed in any of FIGS. 6-14, and perform the methods as described above in any of FIGS. 1-5, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the computer readable code, instructions, or software and any associated data, data files, and data structures in a non-transitory manner and providing the processor or computer readable code, instructions, or software and any associated data, data files, and data structures to a processing device, processor, or computer so that the processing device, processor, or computer can execute the instructions. In one example, the processor or computer readable code, instructions, or software and any associated data, data files, and data structures are distributed over network-coupled computer systems so that the instructions and software and any associated data, data files, and data structures are stored, accessed, and executed in a distributed fashion by the processing device, processor, or computer.

As only an example, a processing device configured to implement a software or processor/computer readable code component to perform an operation A may include a processor programmed to run software or execute processor/computer readable code or instructions to control the processor to perform operation A. In addition, a processing device configured to implement a software or processor/computer readable code component to perform an operation A, an operation B, and an operation C may have various configurations, such as, for example, a processor configured to implement a software or processor/computer readable code component to perform operations A, B, and C; a first processor configured to implement a software or processor/computer readable code component to perform operation A, and a second processor configured to implement a software or processor/computer readable code component to perform operations B and C; a first processor configured to implement a software or processor/computer readable code component to perform operations A and B, and a second processor configured to implement a software or processor/computer readable code component to perform operation C; a first processor configured to implement a software or processor/computer readable code component to perform operation A, a second processor configured to implement a software or processor/computer readable code component to perform operation B, and a third processor configured to implement a software or processor/computer readable code component to perform operation C; a first processor configured to implement a software or processor/computer readable code component to perform operations A, B, and C, and a second processor configured to implement a software or processor/computer readable code component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

As a non-exhaustive example only, an apparatus or system as described herein may be a mobile device, such as a cellular phone, a smart phone, a wearable smart device (such as a ring, a watch, a pair of glasses, a bracelet, an ankle bracelet, a belt, a necklace, an earring, a headband, a helmet, or a device embedded in clothing), a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a high-definition television (HDTV), a DVD player, a Blu-ray player, a set-top box, or a home appliance, or any other mobile or stationary device capable of wireless or network communication. In one example, a wearable device is a device that is designed to be mountable directly on the body of the user, such as a pair of glasses or a bracelet. In another example, a wearable device is any device that is mounted on the body of the user using an attaching device, such as a smart phone or a tablet attached to the arm of a user using an armband, or hung around the neck of the user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is not limited by the detailed description, but further supported by the claims and their equivalents, and all variations within the scope of the claims and their equivalents are to be construed as being included in the disclosure.

What is claimed is:

1. A biometric authentication method comprising:
   extracting, using one or more hardware processors, a same physiological feature from each of two different types of biosignals; and
   determining, using the one or more hardware processors, whether the biosignals are generated from a same living body based on a comparison of the extracted physiological features with a same type of physiological features from different living bodies;
   displaying, using a screen, a result of a positive or negative authentication based on whether the biosignals are generated from the same living body; and
   unlocking, using the one or more hardware processors, secured information in response to the positive authentication, wherein the determining of whether the biosignals are generated from the same live body is based on a comparison between two distribution curves between the same type of physiological features, and calculating a consistent level representing evaluated consistencies between the extracted physiological features using a learner trained based on input physiological feature data of a first sample from biosignals collected simultaneously from a common living body and a second sample from biosignals from different living bodies or at different times, and a preset consistent level.

2. The biometric authentication method of claim 1, further comprising capturing each of the biosignals at a same time using one or more sensors configured to capture biometric features from a body, and determining.

3. The biometric authentication method of claim 2, wherein the capturing of the biosignals includes controlling the one or more sensors to measure the biosignals for a predetermined period of time.

4. The biometric authentication method of claim 1, wherein the biosignals are different types of biosignals from among a human facial image biosignal type, a fingerprint image biosignal type, a palm print image biosignal type, a blood vessel image biosignal type, an iris image biosignal type, a retinal image biosignal type, an ECG signal biosignal type, an EEG signal biosignal type, a photoplethysmogram (PPG) signal biosignal type, a blood pressure signal biosignal type, a heart sound signal biosignal type, an electromagnetic signal associated with a human body biosignal type, a signal associated with a movement of chest or abdominal muscles biosignal type, and a conductive signal of the human body biosignal type.

5. The biometric authentication method of claim 1, wherein the extracting of the physiological features includes extracting, for each of the biosignals, a first same physiological feature type from among a heartbeat physiological feature type, a respiration physiological feature type, a blood pressure physiological feature type, and a body temperature physiological feature type.

6. The biometric authentication method of claim 5, further comprising extracting another same physiological feature from each of the biosignals, including extracting, from each of the biosignals, a second same physiological feature type from among the heartbeat physiological feature type, the respiration physiological feature type, the blood pressure physiological feature type, and the body temperature physiological feature type, different from the first same physiological feature type.

7. The biometric authentication method of claim 6, wherein the determining of whether the biosignals are generated from the same live body comprises:
   calculating the consistent level representing the evaluated consistencies between the extracted physiological features;
   calculating a second consistent level representing evaluated consistencies between the extracted other physiological features; and determining whether the biosignals are generated from the same living body based on both the consistent level and the second consistent level.

8. The biometric authentication method of claim 1, wherein the determining of whether the biosignals are generated from the same live body comprises:
   determining whether the biosignals are generated from the same living body based on the consistent level satisfying a preset condition; and
   setting the preset condition to be an intersection point between the two distribution curves.

9. The biometric authentication method of claim 8, wherein the determining of whether the biosignals are generated from the same living body based on the consistent level satisfying the preset condition comprises determining whether the consistent level satisfies the preset condition based on at least one of a consistent level between a same first physiological feature extracted from each of the biosignals, collected from a body at a same time, and a consistent level between a same second physiological feature extracted from at least two different types of other biosignals collected from one or more other bodies or collected at different times, where the first physiological feature is different from the second physiological feature.

10. The biometric authentication method of claim 8, wherein the calculating of the consistent level comprises calculating the consistent level based on an evaluated relationship between a waveform of each of the extracted physiological features and a collection time in which a predetermined physiological event is collected.

11. The biometric authentication method of claim 10, wherein the physiological event corresponds to a peak or a valley in at least one of the waveforms,
   wherein the consistent level represents a difference or a similarity, and
   wherein the difference is a variance of a deviation of the collection time corresponding to the peak or the valley, and the similarity is a reciprocal of the difference.

12. The biometric authentication method of claim 8, wherein the properties of the extracted physiological features include at least one of a time domain property, a frequency domain property, and a statistical property of the extracted physiological features.

13. The biometric authentication method of claim 12, wherein the time domain property comprises at least one of a moment at which a predetermined physiological event occurs in the extracted physiological features, a moment at which the physiological event changes, a duration of the physiological event, and a signal waveform of each of the extracted physiological features, and
   wherein the frequency domain property comprises a signal frequency spectrum distribution or a signal frequency of each of the extracted physiological features.

14. The biometric authentication method of claim 1, wherein the determining of whether the biosignals are generated from the same living body comprises:
   classifying the biosignals using a classifier based on one or more properties of the extracted physiological features, the classifier using a first type of samples acquired from first biosignals collected at a same time from a same body and a second type of samples acquired from second biosignals collected from one or more other bodies or collected at different times; and
   determining whether the biosignals are generated from the same living body based on a result of the classifying.

15. The biometric authentication method of claim 14, wherein classifying of the biosignals is based on inputting to the classifier the one or more properties of the extracted physiological features, wherein the one or more properties are at least one of a time domain property, a frequency domain property, and a statistical property of the extracted physiological features.

16. The biometric authentication method of claim 15, wherein the time domain property comprises at least one of a moment at which a predetermined physiological event occurs in the extracted physiological features, a moment at which the physiological event changes, a duration of the physiological event, and a signal waveform of each of the extracted physiological features, and
   wherein the frequency domain property comprises a signal frequency spectrum distribution or a signal frequency of each of the extracted physiological features.

17. The biometric authentication method of claim 1, wherein the extracted physiological features are physiological features that vary over time for a living body.

18. The biometric authentication method of claim 1, wherein the extracted physiological features comprise a select one of a heartbeat, a respiration, a blood pressure and a body temperature.

19. The biometric authentication method of claim 1, further comprising performing an authentication or identification of an identity of the living body based on the biosignals being determined to be from the same living body.

20. The biometric authentication method of claim 19, wherein the performing the authentication or identification comprises:
   determining whether identity feature information extracted from at least one of the biosignals or an other biosignal from the living body matches registered identity feature information; and
   performing the authentication or identification of the identity of the living body based on a result of the determining of whether the extracted identity feature information matches the registered identity feature information.

21. The biometric authentication method of claim 20, wherein the extracted identity feature information comprises at least one of a human facial image, a fingerprint image, a palm print image, a blood vessel image, an iris image, a retinal image, an audio signal, a gait feature, a feature of a signature or handwriting, an electrocardiogram (ECG) signal, and an electroencephalogram (EEG) signal.

22. A non-transitory recording medium comprising processor readable code to control at least one processing device to implement the method of claim 1.

23. A biometric authentication apparatus comprising:
   a processor configured to extract a same physiological feature from each of two different types of biosignals and to determine whether the biosignals are generated from a same living body based on a comparison of the extracted physiological features with a same type of physiological features from different living bodies, and a calculation of a consistent level representing evaluated consistencies between the extracted physiological features using a learner trained based on input physiological feature data of a first sample from biosignals collected simultaneously from a common living body and a second sample from biosignals from different living bodies or at different times, and a preset consistent level; and
   a screen configured to display a result of a positive or negative authentication based on whether the biosignals are generated from the same living body, and wherein the processor unlocks secured information in response to the positive authentication, wherein the processor determines whether the biosignals are generated from the same live body based on comparing a level between the extracted physiological features with two distribution curves between the same type of physiological features.

24. The biometric authentication apparatus of claim 23, further comprising one or more sensors configured to capture biometric features from a body, the processor being further configured to control a capturing of each of the biosignals at a same time using the one or more sensors.

25. The biometric authentication apparatus of claim 24, wherein the processor is configured to control the one or more sensors to measure the biosignals for a predetermined period of time.

26. The biometric authentication apparatus of claim 23, further comprising a communication device to communicate with one or more remote sensors configured to capture biometric features from a body, the processor being further configured to control or selectively receive a measuring of each of the biosignals, measured at a same time by the one or more sensors.

27. The biometric authentication apparatus of claim 23, wherein the biosignals are each analog or digital information respectively representing a different physical characteristic or behavioral characteristic of a body.

28. The biometric authentication apparatus of claim 27, wherein, to determine whether the biosignals are generated from the same live body, the processor is configured to evaluate consistencies between the extracted physiological features and determines whether the biosignals are generated from the same living body based on the evaluated consistencies.

29. The biometric authentication apparatus of claim 28, wherein the processor is configured to:
   extract an other same physiological feature from the biosignals;
   evaluate consistencies between the extracted other physiological features; and
   determine whether the biosignals are generated from the same living body based on the evaluated consistencies between the extracted physiological features and the evaluated consistencies between the extracted other physiological features.

30. The biometric authentication apparatus of claim 28, wherein the processor is configured to:
   determine whether identity feature information extracted from at least one of the biosignals or an other biosignal from the living body matches registered identity feature information; and
   perform an authentication or identification of the identity of the living body based on the determination by the processor of whether the biosignals are generated from the same living body and the determination of whether the extracted identity feature information matches the registered identity feature information.

* * * * *